United States Patent [19]

Neurath et al.

[11] Patent Number: 5,204,096

[45] Date of Patent: Apr. 20, 1993

[54] PRE-S GENE CODED PEPTIDE HEPATITIS B IMMUNOGENS, VACCINES, DIAGNOSTICS, AND SYNTHETIC LIPID VESICLE CARRIERS

[75] Inventors: Alexander R. Neurath, New York, N.Y.; Stephen B. H. Kent, Pasadena, Calif.

[73] Assignees: New York Blood Center, Inc., New York, N.Y.; California Institute of Technology, Pasadena, Calif.

[21] Appl. No.: 338,028

[22] Filed: Apr. 14, 1989

Related U.S. Application Data

[60] Division of Ser. No. 698,499, Feb. 5, 1985, Pat. No. 4,847,080, which is a continuation-in-part of Ser. No. 587,090, Mar. 7, 1984, abandoned.

[51] Int. Cl.$^5$ .................. A61K 39/12; A61K 37/02
[52] U.S. Cl. ........................... 424/89; 424/88; 424/86; 424/85.8; 530/324; 530/328; 530/329; 530/350; 514/13; 514/14; 514/15; 514/17
[58] Field of Search ............ 424/89, 88, 86, 85.8; 530/324, 328, 329, 350; 514/13, 14, 15, 17

[56] References Cited

U.S. PATENT DOCUMENTS

| | | | |
|---|---|---|---|
| 4,415,491 | 11/1983 | Vyas | 424/86 |
| 4,428,941 | 1/1984 | Galibert et al. | 435/68 |
| 4,599,230 | 6/1986 | Milich et al. | 424/88 |
| 4,683,136 | 4/1987 | Milich et al. | 424/89 |
| 4,816,564 | 3/1989 | Ellis et al. | 424/89 |
| 4,935,235 | 6/1990 | Rutler et al. | 424/88 |

FOREIGN PATENT DOCUMENTS

| | | |
|---|---|---|
| 0020251 | 10/1980 | European Pat. Off. |
| 0171260 | 2/1986 | European Pat. Off. |
| 1414480 | 11/1975 | United Kingdom |

OTHER PUBLICATIONS

Ono et al. "The complete nucleotide sequence of the cloned hepatitis B virus DNA; subtype adr and adw" Nucleic acids Research, vol. 11, No. 6, pp. 1747–1767, 1983.
Valenzuela et al, "Nucleotide sequence of the gene coding for the major protein of hepatitis B surface antigen" Nature, vol. 280, pp. 815–819, 1979.
Chemical Abstracts, vol. 100, No. 19, May 7, 1984, p. 139, ref. No. 151196c; Columbus, OH, US & JP-A-58 194 897 (Takeda Chem. Ind. Ltd.) Dec. 11, 1983.
Journal of Virology, vol., 46, No. 2, May 1983, pp. 626–628; Am. Soc. for Microbiology, US W. Stibbe et al.; "Structural relationship between minor and major proteins of Hepatitis B surface antigen."
Gastroenterology, vol. 85, No. 2, 1983, pp. 268–274; Am. Gastroenterological Ass., US A. Machida et al.: "A Hepatitis B surface antigen polypeptide (P31) with the receptor for polymerized human as well as chimpanzee albumins."

(List continued on next page.)

Primary Examiner—Johnnie R. Brown
Assistant Examiner—Abdel A. Mohamed
Attorney, Agent, or Firm—Sprung Horn Kramer & Wood

[57] ABSTRACT

A hepatitis B vaccine containing a peptide with an amino acid chain of at least six consecutive amino acids within the pre-S gene coded region of the envelope of hepatitis B virus. The vaccine being free of an amino acid sequence corresponding to the naturally occurring envelope proteins of hepatitis B virus and a physiologically acceptable diluent. The peptide being free or linked to a carrier. The carrier being a conventional carrier or a novel carrier including a lipid vesicle stabilized by cross-linking and having covalently bonded active sites on the outer surface thereon. Such novel carrier being useful not only to link the novel peptide containing an amino acid chain with amino acids within the pre-S gene coded region of the surface antigen or hepatitis B virus, but can also be used to bind synthetic peptide analogues of other viral proteins, as well as bacterial, allergen and parasitic proteins of man and animals. The peptides of the invention can be utilized in diagnostics for the detection of antigens and antibodies.

52 Claims, 14 Drawing Sheets

OTHER PUBLICATIONS

Proc. Natl. Acad. Sci. USA, vol. 78, No. 6, Jun. 1981, pp. 3824–3828; US, T. P. Hopp et al.; "Prediction of protein antienic determinants from amino acid sequences".

Experientia, vol. 38, No. 5, May 1982, pp. 629–630; Basel, CH P. K. DAS et al.: "Liposomes as immulogical carriers for the preparation of antimannosyl antibodies." pp. 629, column 1, lines 12–13, column 2, lines 1–2.

Gastroenterology, vol. 86, 1984, pp. 910–918; Am. Gastroenterological Ass., US A. Machida et al.: "A polypeptide contanining 55 amino acid residues coded by the pre-S region of Hepatitis B virus deoxyribonucleic acid bears the receptor for polymerized human as well as chimpanzee albumins."

Science, vol. 224, Apr. 27, 1984, pp. 392–395, A. R. Neurath et al.: "Location and chemical synthesis of a pre-S gene coded immunodominant epitope of Hepatitis B virus".

Immunodominant Epitope of Hepatitis B virus, vol. 101, p. 5405 y, (1984).

Chemical Abstracts; Machida et al. A polypeptide containing 55 amino acid residues coded by the pre-S region of hepatitis B virus deoxyribonucleic acid bears the receptor for polymerized human as well as chimpanzee albumins, vol. 101, p. 34692 w, (1984).

Chemical Abstracts; Neurath et al. Location and chemical synthesis of a pre-S gene coded.

A. R. Mitchell, S. B. H. Kent, M. Engelhard and R. B. Merrifield, *J. Org. Chem.*, 43, 2845–2852, (1978).

S. B. H. Kent, M. Riemen, Marie LeDoux, and R. B. Merrifield, *Methods in Protein Sequence Analysis*, pp. 205–213, Brookhaven Press, Brookhaven, N.Y.), in press, (1981).

S. B. H. Kent, *Biomedical Polymers*, eds, E. P. Goldberg and A. Nakajima (Academic Press, New York), 213–242, (1980).

W. Szmuness, *Prog. Med. Virol.*, 24, 40 (1978).

R. P. Beasley, L.-Y. Hwang, C.-C. Ling, C.-S. Chien, *Lancet*, Nov., 21.

Krugman, *Viral Hepatitis: Laboratory and Clinical Science*, F. Deinhardt, J. Deinhardt, Eds., Marcel Dekker, Inc., New York-Basel, 1983, pp. 257–263.

B. S. Blumberg, *Science*, 197, 17, (1977).

P. Tiollais, P. Charnay, G. N. Vyas, *Science*, 213, 406, (1981).

Williams, *Am. J. Med. Sci.*, 270, 165 (1975).

W. Szmuness, C. E. Stevens, E. J. Harley, E. A. Zang, J. J. Alter, P. E. Taylor, A. DeVera, G. T. S. Chen, A. Kellner, et al., *N. Engl. J. Med.*, 307, 1481; (1982).

J. W.-K. Shih, J. L. Gerin, *J. Immunol.*, 115,634 (1975).

J. W.-K. Shih, P. L. Tan, J. L. Gerin, *J. Immunol.*, 120,520 (1978).

S. Mishiro, M. Imai, K. Takahashi, A. Machida, T. Gotanda, Y. Miyakawa, M. Mayumi, J. Immunol., 124, 1589, (1980).

G. R. Dressman, R. Chairez, M. Suarez, F. B. Hollinger, R. J. Courtney, J. L. Melnick, *J. Virol.*, 16, 508, (1975).

N. Williams, *Nature*, 306, 427, (1983).

A. Machida, S. Kishimoto, H. Ohnuma, H. Miyamoto, K. Baba, K. Oda, T. Nakamura, Y. Miyakawa, M. Mayumi, *Gastroenterology*, 85, 268, (1983).

Nima, H. L., Houghten, R. A., Walker, L. E., Reisfeld, R. A., Wilson, I. A., Hogle, J. M. and Lerner, R. A., "Generation of Protein-Reactive Antibodies By Short Peptides Is An Event Of High Frequency: Implications For The Structural Basis Of Immune Recognition", *Proceedings of the National Academy of Sciences USA*, 80 4949–4953, (1983).

Kennedy, R. C., Dressman, G. R., Sparrow, J. T., Culwell, A. R., Sanchez, Y., Ionescu-Matiu, I., Hollinger, R. B. and Melnick, J. L., "Inhibition Of A Common Human Anti-Hepatitis B. Surface Antigen Idiotype By A Cyclic Synthetic Peptide", *Journal of Virology*, 46, 653–655, (1983).

Dressman, G. R., Sanchez, Y., Ionescu-Matiu, I., Sparrow, J. T., Six. H. R., Peterson, D. L. Hollinger, F. B. and Melnick, J. L., "Antibody To Hepatitis B. Surface Antigen After A Single Inoculation Of Uncoupled Synthesis HBsAg Peptides", *Nature*, 295, 158–160, (1982).

G. N. Vyas, K R. Rao, A. B. Ibrahim, *Science*, 178, 1300, (1972).

G. R. Dressman, F. B. Hollinger, R. M. McCombs, J. L. Melnick, *J. Gen. Virol.*, 19, 129, (1973).

A. R. Neurath, N. Strick, *J. Med. Virol.*, 6, 309, (1980).

A. R. Neurath, S. B. H. Kent, and N. Strick, *Proc. Natl. Acad. Sci. USA* 79, 7871 (1982).

F. Galibert, T. N. Chen, E. Mandart, *J. Virol.*, 41 51, (1982).

Oku, N. Scheerer, J. F., and MacDonald, R. C., "Preparation of Giant Liposomes", *Biochimica et Biophysica Acta*, 692, 384–388, (1982).

(List continued on next page.)

OTHER PUBLICATIONS

Dancey, G. F., Yasuda, T. and Kinsky, S. C., "Effect of Liposomal Model Membrane Composition On Immunogenicity", *The Journal Of Immunology*, 120, 1109–1113, (1978).

Alkan, S. S., Nitecki, D. E. and Goodman, J. W., "Antigen Recognition And The Immune Response: The Capacity of 1-Tryosine-Azobenzenezrsonate To Serve As A Carrier For A Macromolecular Hapten", *The Journal of Immunology*, 107, 353–358, (1971).

Alkan, S. S., Williams, E. B., Nitecki D. E. and Goodman, J. W., "Antigen Recognition And The Immune Response. Hurmoral And Cellular Immune Responses To Small Mono— And Bifunctional Antigen Molecules", *The Journal Of Experimental Medicine*, 135, 1228–1246, (1972).

V. P. Torchilin, V. S. Goldmacher and V. N. Smirnov, "Comparative Studies On Covalent And Noncovalent Immobilization of Protein Molecules On The Surface Of Liposomes", *Biochemical And Biophysical Research Communications*, vol. 85, No. 3, 1978, pp. 983–990.

V. K. Jansons and P. L. Mallett, "Targeted Liposomes: A Method For Preparation And Analysis, *Analytical Biochemistry III*, pp. 54–59, 1981.

F. J. Martin and D. Papahadjopoulos, "Irreversible Coupling Of Immonogobulin Fragments To Performed Vesicles", *The Journal Of Biological Chemistry*, vol. 257, No. 1, Jan. 10, 1982, pp. 286–288.

D. Gerlier, "Liposomes As A Tool To Study The Role Of Membrane Presentation In The Immunogenicity Of MVLV-Related Tumor Antigen", *J. Immunol.*, 131, 485, (1983).

L. D. Leserman, "Targeting To Cells Of Fluorescent Liposomes Covalently Coupled With Monoclonal Antibody Or Protein A", *Nature*, 288, 602, (1980).

M. Tomasi, "Conjugation Of Specific Antibodies To Sendai Virus Particles" A New Tool For Targeting Of Fusogenic Vesicles", *Federation of European Biological Letters*, 143, 252, (1982).

P. N. Shek, "Immune Response Mediated By Liposome-Associated Protein Antigens", *Immunology*, 45, 349, (1982).

F. J. Martin, "Immunospecific Targeting Of Liposomes To Cells. A Novel And Efficient Method for Covalent Attachment of Fab' Fragments Via Disulfide Bonds", *Biochemistry*, 20, 4229, (1981).

M. R. Mansk, "Targeting Of Lipod Vesicles", *Proc. Natl. Acad. Sci.* 77, 4430, (1980).

FIG. 2

PRE-S GENE CODED PEPTIDE HEPATITIS B IMMUNOGENS, VACCINES, DIAGNOSTICS, AND SYNTHETIC LIPID VESICLE CARRIERS

CROSS REFERENCE TO RELATED APPLICATION

This is a division of application Ser. No. 06/698,499, filed Feb. 5, 1985, now U.S. Pat. No. 4,847,080, which is a continuation-in-part application of patent application Ser. No. 587,090, filed Mar. 7, 1984, now abandoned.

BACKGROUND OF THE INVENTION

The present invention concerns pre-S gene coded hepatitis B immunogens, vaccines and diagnostics. More especially, this invention concerns novel pre-S gene coded peptides and novel carriers, particularly carriers for pre-S gene coded peptides. Even more especially, the present invention relates to synthetic pre-S gene coded peptides covalently linked to lipid vesicle carriers.

There are approximately 600,000 persistent carriers of hepatitis B virus (HBV) in the United States; the estimated total number of carriers in the world is 200 million. A considerable portion of HBV carriers have chronic liver disease. The involvement of HBV in liver cancer has been demonstrated (W. Szmuness, *Prog. Med. Virol.* 24, 40 (1978) and R. P. Beasley, L. -Y. Hwang, C. -C. Ling, C. -S. Chien, *Lancet* Nov., 21, 1129 (1981)).

HBV infections thus represent a major public health problem worldwide. Already available vaccines (S. Krugman, in *Viral Hepatitis: Laboratory and Clinical Science*, F. Deinhardt, J. Deinhardt, Eds., Marcel Dekker, Inc., New York-Basel, 1983, pp. 257-263) produced from the serum of HBV carriers, because of limited resources and production costs involved, do not provide the appropriate means to control and eradicate the disease worldwide. There is hope, however, that this may be accomplished by vaccines based on recombinant DNA technology and/or synthetic peptides.

The biology, structure and immunochemistry of HBV and the genetic organization of its DNA genome have been reviewed (B. S. Blumberg, *Science*, 197 17, (1977)). The cloning and sequencing of the genome of several hepatitis virus (HBV) isolates led to the elucidation of the genetic structure of the viral DNA (P. Tiollais, P. Charnay, G. N. Vyas, *Science*, 213, 406, (1981)).

The immunologic markers of HBV infection include the surface antigen (HBsAg), the core antigen (HBcAg), the "e" antigen (HBeAg) and their respective antibodies. Antibodies against HBsAg are protective against HBV infection.

Several antigenic subtypes of HBV and of subviral approximately 22 nm diameter particles (hepatitis B surface antigen; HBsAg) have been recognized (G. Le Bouvier, A. Williams, *Am. J. Med. Sci.*, 270, 165 (1975)). All of these subtypes (for example, ayw, adyw, adw2, adw and adr) share common (group-specific) envelope epitopes, the immune response against which appears sufficient for protection against infection by any of the virus subtypes (W. Szmuness, C. E. Stevens, E. J. Harley, E. A. Zang, H. J. Alter, P. E. Taylor, A. DeVera, G. T. S. Chen, A. Kellner, et al., *N. Engl. J. Med.*, 307, 1481, (1982)).

The physical structure and proposed genetic organization of the HBV genome are described by Tiollais et al, 1981, supra at pp. 408-409. There are two DNA strands, namely the long (L) strand and the short (S) strand. The L strand transcript has four open reading frame regions which are termed (S+pre-S), C, P and X.

The open reading frame region (S+pre-S) corresponds to the envelope (env) gene of HBV DNA and codes for a family of proteins found in the HBV envelope and in virus related particles.

A schematic representation of the potential translation products of the env gene(s) of HBV DNA is as follows:

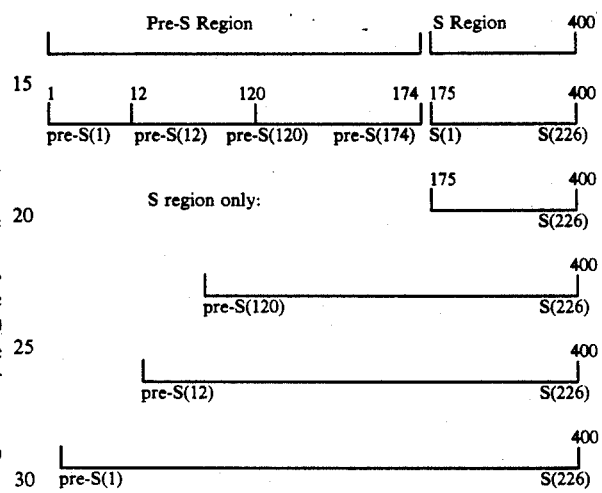

The numbers in the above schematic refers to amino acids (AA). A translation initiation site at Met 1 exists for the adw$_2$ and adr substypes only. The first amino acid for the other subtypes correspond to position pre-S 12.

Hereinafter, amino acid sequences corresponding to the pre-S region (env 1 to 174) are designated with the prefix "pre-S" and amino acid sequences corresponding to the S region (env 175 to 400) are designated by the prefix "S". In the env gene product representation, the S region spans amino acids 175 to 400 as compared to amino acids 1 to 226 in the "S region only" representation.

In the above schematic, the pre-S region is defined by amino acid sequence positions pre-S 1 to amino acid sequence position pre-S 174. The S region is defined by sequence positions S 1 (amino acid 175 of the open reading frame and adjacent to pre-S 174) to sequence position S 226 (amino acid 400 of the open reading frame). The s-gene product (S-protein) consists of this 226 amino acid sequence.

The epitope(s) essential for eliciting virus-neutralizing antibodies have not yet been unambiguously defined. It has been reported that the group-specificity is represented by a complex of determinants located on each of the two major approximately 22 and approximately 26 kilodalton constituent proteins (P22 and P26) of the virus envelope and of the hepatitis B surface antigen (HBsAg). See J. W. -K. Shih, J. L. Gerin, *J. Immunol.*, 115, 634, (1975); J. W. -K. Shih, P. L. Tan, J. L. Gerin, *J. Immunol.*, 120, 520, (1978); S. Mishiro, M. Imai, K. Takahashi, A. Machida, T. Cotanda, Y. Miyakawa, M. Mayumi, *J. Immunol.*, 124, 1589, (1980); and G. R. Dreesman, R. Chairez, M. Suarez., F. B. Hollinger, R. J. Courtney, J. L. Melnick, *J. Virol.*, 16, 508, (1975).

These proteins have identical amino acid sequences coded for by the S-gene of HBV DNA (Tiollais et al, supra), but the larger protein also carries carbohydrate chains. Peptides corresponding to selected segments of the S-gene product were synthesized and shown to elicit antibodies to HBsAg (anti-HBs). However, immunization of chimpanzees with these peptides resulted in only partial protection against HBV infection (N. Williams, *Nature*, 306, 427, (1983)).

It has been reported recently that the minor glycoprotein components of HBsAg with $M_r$ of approximately 33 and approximately 36 kilodaltons (P33, P36) are coded for HBV DNA and contain the sequence of P22 (226 amino acids corresponding to the S region) and have 55 additional amino acids at the amino-terminal part which are coded by the pre-S region of the env gene(s) of HBV DNA. See W. Stibbe, W. H. Gerlich, *Virology*, 123, 436, (1982); M. A. Feitelson, P. L. Marion, W. S. Robinson, *Virology*, 130, 76, (1983); W. Stibbe, W. H. Gerlich, *J. Virol.*, 46, 626, (1983); and A. Machida, S. Kishimoto, H. Ohnuma, H. Miyamoto, K. Baba, K. Oda, T. Nakamura, Y. Miyakawa, M. Mayumi, *Gastroenterology*, 85, 268, (1983). Machida et al describe an amino acid sequence composition as a receptor for polymerized serum albumin.

Heretofore, amino acid sequences coded for by the pre S region of the hepatitis B virus DNA were virtually completely ignored for purposes of producing synthetic vaccines. The hepatitis B vaccine currently in use in the United States lacks the pre-S gene coded sequences (and therefore does not elicit antibodies to such sequences) and thus elicits an immune response to the HBV envelope which is incomplete as compared with that occurring during recovery from natural infection.

The generation of antibodies to proteins by immunization with short peptides having the amino acid sequence corresponding to the sequence of preselected protein fragments appears to be a frequent event (Nima, H. L., Houghten, R. A., Walker, L. E., Reisfeld, R. A., Wilson, I. A., Hogle, J. M. and Lerner, R. A., "Generation of Protein-Reactive Antibodies By Short Peptides Is An Event Of High Frequency: Implications For The Structural Basis Of Immune Recognition", *Proceedings of the National Academy of Sciences USA*, 80, 4949–4953, (1983)). Nevertheless, the generation of antibodies which recognize the native protein may depend on the appropriate conformation of the synthetic peptide immunogen and on other factors not yet understood. See Pfaff, E., Mussgay, M., Böhm, H. O., Schulz, G. E. and Schaller, H., "Antibodies Against A Preselected Peptide Recognize And Neutralize Foot And Mouth Disease Virus", *The EMBO Journal*, 7, 869–874, (1982); Neurath, A. R., Kent, S. B. H. and Strick, N., "Specificity Of Antibodies Elicited By A Synthetic Peptide Having A Sequence In Common With A Fragment Of A Virus Protein, The Hepatitis B Surface Antigen," *Proceedings Of The National Academy Of Sciences USA*, 79, 7871–7875, (1982); Ionescu-Matiu, I., Kennedy, R. C., Sparrow, J. T., Culwell, A. R., Sanchez, Y., Melnick, J. L. and Dreesman, G. R., "Epitopes Associated With A Synthetic Hepatitis B Surface Antigen Peptide", *The Journal Of Immunology*, 130, 1947–1952, (1983); and Kennedy, R. C., Dreesman, G. R., Sparrow, J. T., Culwell, A. R., Sanchez, Y., Ionescu-Matiu, I., Hollinger, F. B. and Melnick, J. L. (1983); "Inhibition Of A Common Human Anti-Hepatitis B Surface Antigen Idiotype By A Cyclic Synthetic Peptide," *Journal of Virology*, 46, 653-655, (1983). For this reason, immunization with synthetic peptide analogues of various virus proteins has only rarely resulted in production of virus-neutralizing antisera comparable to those elicited by the viruses (virus proteins) themselves (Pfaff et al., 1982, supra). Thus, the preparation of synthetic immunogens optimally mimicking antigenic determinants on intact viruses remains a challenge.

Replacement of commonly used protein carriers, namely keyhole limpet hemocyanin (KLH), albumin, etc., by synthetic carriers, represents part of such challenge. Although recent reports indicate that free synthetic peptides can be immunogenic Surface Antigen After A Single Inoculation Of Uncoupled Synthetic HBsAg Peptides" *Nature*, 295, 158–160, (1982), and Schmitz, H. E., Atassi, H., and Atassi, M. Z., "Production Of Monoclonal Antibodies To Surface Regions That Are Non-Immunogenic In A Protein Using Free Synthetic Peptide As Immunogens: Demonstration With Sperm-whale Myoglobin", *Immunological Communications*, 12, 161-175, (1983)), even in these cases the antibody response was enhanced by linking of the peptides to a protein carrier (Sanchez, Y., Ionescu-Matiu, I., Sparrow, J. T., Melnick, J. L., Dreesman, G. R., "Immunogenicity Of Conjugates And Micelles Of Synthetic Hepatitis B Surface Antigen Peptides", *Intervirology*, 18, 209-213, (1982)).

For commonly used protein carriers there is a strong immune response to the carrier, as well as the synthetic peptide. Thus, it would be advantageous to evoke an anti-HBs response with peptides by use of non-protein carriers, which themselves do not evoke an antibody response.

The possible use of several distinct vaccines in prophylaxis would be facilitated by the availability of fully synthetic immunogens.

DEFINITIONS
Amino Acid Code Words (as appearing in FIG. 2)

| | | |
|---|---|---|
| D | Asp | aspartic acid |
| N | Asn | asparagine |
| T | Thr | threonine |
| S | Ser | serine |
| E | Glu | glutamic acid |
| Q | Gln | glutamine |
| P | Pro | proline |
| G | Gly | glycine |
| A | Ala | alanine |
| C | Cys | cysteine |
| V | Val | valine |
| M | Met | methionine |
| I | Ile | isoleucine |
| L | Leu | leucine |
| Y | Tyr | tyrosine |
| F | Phe | phenylalanine |
| W | Trp | tryptophane |
| K | Lys | lysine |
| H | His | histidine |
| R | Arg | arginine |
| HBV | | hepatitis B virus |
| HBsAg | | hepatitis B surface antigen |
| DNA | | deoxyribonucleic acid |

SUMMARY OF THE INVENTION

The applicants have found that antibodies to the pre-S protein appear early in the course of hepatitis B infection and probably play the role of antibodies eliminating HBV from the circulation and thus interrupting further spread of the infection. Antibodies to the pre-S protein are likely to represent virus-neutralizing antibodies. The failure of some hepatitis B vaccines to elicit such antibodies may be of considerable biological significance, as indicated by poor immunoprophylactic effects elicited by such vaccines in some populations, despite a detectable immune response to the S-protein.

Applicants have discovered that amino acid sequences coded for by the pre-S region of the env gene of hepatitis B virus (HBV) DNA carry dominant antigenic determinants common to intact and denatured HBsAg. Applicants have found that immuno-dominant disulfide bond-independent epitopes recognized by human antibodies to hepatitis B virus (HBV) exist within proteins containing amino acid sequences coded by the pre-S region of HBV DNA, and more particularly within proteins containing an N-terminal portion (coded for the pre-S region of HBV DNA) having an N-terminal methionine at amino acid sequence position pre-S 120. Applicants further discovered that peptides corresponding to amino acid sequences in the pre-S region, and more particularly in the aforementioned region starting at amino acid 120 of the env gene open reading frame, inhibit the reaction between human anti-HBs and P33 (P36), are highly immunogenic, and elicit high levels of group-specific antibodies against HBsAg and HBV. The immunogenicity of such peptides is enhanced by covalent linking to novel lipid vesicle (liposome) carriers also discovered by applicants.

Glutaraldehyde-fixed liposomes were found by applicants to be preferred carriers for the peptides of the invention for inducing anti-HBs.

The present invention thus concerns a hepatitis B peptide immunogen including a peptide containing an amino acid chain corresponding to at least six consecutive amino acids within the pre-S gene coded region of the envelope of HBV. The hepatitis B peptide immunogen is free of an amino acid chain corresponding to the naturally occurring envelope proteins of hepatitis B virus.

The naturally occurring envelope proteins of hepatitis B virus include the following:

(1) a full length translational product of the env gene of HBV, i.e., for $adw_2$ and adr pre-S(1–174)+S(1–75–400)=400 amino acids, for ayw, adyw and adw pre-S(12–174)+S(1–226)=389 amino acids (env 12–400);

(2) pre-S(120–174)+S(175–400)=281 amino acids (env 120–400)=terminal 55 amino acids in the pre-S region+226 amino acids comprising the entire S region (the corresponding proteins approximately 33 and 36 kD in size (P33 and P36), and differing from each other in the extent of glycosylation); and (3) S(1–226)=226 amino acids, i.e., the entire S region (env 175–400); representing the approximately 22 and 26 kD major constituents of the HBV envelope (P22 and P26) in their non-glycosylated and glycosylated forms (the "S-protein").

In an embodiment of the hepatitis B peptide immunogen of the present invention, the corresponding chain of amino acids lies between the sequence positions pre-S 120 and pre-S 174. In another embodiment of the invention, the chain of amino acids is between sequence positions pre-S 1 and pre-S 120. In a further embodiment of the invention, the corresponding chain of amino acids includes the methionine amino acid at sequence position pre-S 120. In still another embodiment, the chain of amino acids is an amino acid chain containing at least 26 amino acids in the pre-S region. Still further, the chain of amino acids containing at least 26 amino acids can correspond to a chain of at least 26 consecutive amino acids disposed between sequence position pre-S 120 and sequence position pre-S 174. Generally the peptide has no more than 280 amino acids, preferably no more than 225 amino acids, more preferably no more than 174 amino acids, even more preferably no more than 100 amino acids, and still more preferably, no more than 50 amino acids. The vaccine of the present invention can be composed solely of a peptide, or preferably of a peptide joined to a carrier. Such carrier can be a conventional carrier, or a novel carrier according to the present invention as described hereinbelow.

The hepatitis B peptide immunogen of the present invention is free of any serum proteins, e.g., blood serum proteins.

The present invention also concerns a hepatitis B vaccine including a peptide containing an amino acid chain corresponding to at least six consecutive amino acids within the pre-S gene coded region of the envelope of HBV, and a physiologically acceptable diluent, e.g., phosphate buffered saline. The hepatitis B peptide vaccine being free of an amino acid chain corresponding to the naturally occurring envelope proteins of hepatitis B virus.

The present invention is also directed to a novel carrier for peptides. In a particularly preferred embodiment of the present invention, the hepatitis B vaccine containing an amino acid chain corresponding to a chain of amino acids in the pre-S region is linked to a carrier via active sites on the carrier. Still more preferred, the carrier is a lipid vesicle carrier. Even more preferred, the lipid vesicle carrier is stabilized by cross-linking.

The carrier of the present invention includes a lipid vesicle stabilized by cross-linking and having covalently bonded active sites on the outer surface thereof. The synthetic peptide is bonded via such active sites on the carrier to the outer surface of the lipid vesicle. Such active sites include —COOH, —CHO, —NH₂ and —SH. Such stabilization by cross-linking is accomplished by a stabilizing agent such as an aldehyde having at least two functional groups, such as a bifunctional aldehyde, for example, glutaraldehyde. The carrier of the present invention is chemically cross-linked with pendant functional groups.

The present application also concerns diagnostic methods. The present invention relates to processes for detecting the presence of either pre-S gene coded-hepatitis B antigens or antibodies in a serum.

Antibodies to the synthetic peptides disclosed herein can be detected in samples by a process which comprises:

a) contacting the sample with a solid substrate coated with a non-labelled peptide containing an amino acid chain corresponding to at least six consecutive amino acids within the pre-S gene coded region of the envelope of HBV, the peptide free of an amino acid sequence corresponding to the naturally occurring envelope proteins of hepatitis B virus, incubating and washing said contacted sample;

b) contacting the incubated washed product obtained from step a above with a labelled peptide containing an amino acid chain corresponding to at least six consecutive amino acids within the pre-S gene coded region of the envelope of HBV, said peptide free of an amino acid sequence corresponding to the naturally occurring envelope protein of hepatitis B virus, incubating and washing the resultant mass; and c) determining the extent of labelled peptide present in the resultant mass obtained by step b above.

Such a process is normally performed using a solid substrate which is substantially free of available protein binding sites. Such as by binding sites unbound by unlabelled peptide with a protein binding site occupier, e.g., albumin.

Another process for detecting such antibodies comprises:

a) contacting the sample with a solid substrate coated with a non-labelled peptide containing an amino acid chain corresponding to at least six consecutive amino acids within the pre-S gene coded region of the envelope of HBV, the peptide free of an amino acid sequence corresponding to the naturally occurring envelope proteins of hepatitis B virus, incubating and washing said contacted sample;

b) contacting the incubated washed product obtained from step a above with labelled antibody to human or animal immunoglobulin product by contact with an immunogen comprising a peptide corresponding to at least six consecutive amino acids within the pre-S gene coded region of the envelope of HBV, the peptide immunogen free of an amino acid sequence corresponding to the naturally occurring envelope proteins of hepatitis B virus, incubating and washing the contacted sample, and c) determining the extent of labelled antibody present in the resultant mass of step b.

HBV or HBsAg can be detected in a sample by a process which comprises:

a) contacting a first portion of a composition containing an antibody produced by introducing into an animal or human an immunogen comprising a peptide corresponding to at least six consecutive amino acids within the pre-S gene coded region of the envelope of HBV, the peptide immunogen free of an amino acid sequence corresponding to the naturally occurring envelope proteins of hepatitis B virus, with a mixture of said sample and the immunogen which has been labelled, incubating and washing the first portion;

b) contacting a second portion of the composition containing antibody with the same amount of the labelled immunogen in an antigen free control, incubating and washing the second portion;

c) adding the same amount of Staphylococci bearing protein A to each of the compositions of steps a and b above, incubating both of the compositions, centrifuging each of the compositions and separating liquid from the solids therein;

d) determining the extent of labelled immunogen in each of the resultant compositions from step c above, and e) comparing the relative amount of labelled immunogen in each such that if the activity of the resultant composition containing the first portion is less than the activity for the resultant composition of the second portion, then the sample contains HBV or HBsAg.

The synthetic immunogens can be used in general in both sandwich type immunoassays and competition type immunoassays, such as those immunoassays in which antigen in the sample competes with labelled immunogen for antibody.

These and other suitable immunoassay schemes for use in connection with the synthetic immunogens of this invention and antibodies thereto are disclosed in copending application Ser. No. 426,309, filed Sep. 29, 1982, now U.S. Pat. No. 4,591,522, issued May 27, 1986, entitled Labelled Peptides As Diagnostic Reagents, assigned to one of the assignees hereof, the disclosure of which is hereby incorporated herein by reference.

The present invention also concerns a diagnostic test kit for detecting hepatitis B virus in sera comprising a) antibodies to a peptide containing an amino acid chain corresponding to at least six consecutive amino acids within the pre-S gene coded region of the envelope of HBV, the peptide being free of an amino acid chain corresponding to the naturally occurring envelope proteins of hepatitis B virus, attached to a solid support, c) labelled antibodies to the peptide or to hepatitis B virus.

The kit can comprise a set of instructions for effecting an immunoassay wherein the effect of formation of an immune complex is revealed by said labelled antibody.

The present invention also concerns a diagnostic kit for detecting the presence of antibodies to pre-S gene coded antigens of hepatitis B virus in a test sample comprising a) a given amount of a peptide containing an amino acid chain corresponding to at least six consecutive amino acids within the pre-S gene coded region of the envelope of HBV, the peptide being free of an amino acid chain corresponding to the naturally occurring envelope proteins of hepatitis B virus. The peptide is attached to a solid support, e.g., a water insoluble solid support.

b) labelled antibodies, e.g., radiolabeled or enzyme labelled, to human IgG and/or IgM.

The kit can comprise a set of instructions for effecting an immunoassay, wherein the extent of formation of an immune complex is revealed by said labelled antibodies.

In a particular aspect, the present invention concerns a process for the detection of antigens coded for the pre-S gene in sera of HBV infected humans and certain animals, for example, chimpanzees, comprising the following steps:

(a) coating a solid substrate with antibodies to a peptide having an amino acid chain corresponding to at least six consecutive amino acids within the pre-S gene of HBV DNA, the peptide being free of an amino acid sequence corresponding to the naturally occurring envelope proteins of HBV, (b) washing the coated substrate;

(c) contacting the washed coated substrate, e.g., polystyrene beads; with a protein-containing solution;

(d) washing the substrate from step c;

(e) incubating the substrate from step d with a sample suspected to contain HBV or HBsAg;

(f) washing the substrate from step e;

(g) adding radiolabeled or enzyme-labeled antibody, the antibody being an antibody to the peptide or HBsAg;

(h) incubating the substrate from step g;

(i) washing the substrate from step h; and (j) subjecting the substrate of step i to counting in a gamma counter, or measuring its enzymatic activity.

The above process can be conducted using ELISA techniques rather than RIA detection techniques.

In a particular embodiment, the present invention also relates to a process for the detection of antibodies to proteins coded for by the pre-S region of hepatitis B virus DNA, comprising the following steps:

(a) adsorbing on a solid substrate containing binding sites thereon, e.g., polystyrene beads, a peptide having an amino acid sequence corresponding to at least six consecutive amino acids within the pre-S gene coded region of the HBV envelope, the peptide being free of an amino acid sequence corresponding to the naturally occurring envelope proteins of hepatitis B virus, (b) contacting the substrate from step a with a material to saturate the binding sites thereon, (c) washing the substrate from step b, (d) contacting the substrate from step c with a specimen comprising human sera, (e) incubating the resultant mass of step d, (f) washing the resultant mass of step e, (g) adding radiolabeled antibodies to human IgG or IgM to the resultant mass of step f to form a second resultant mass, (h) subjecting the second resultant mass of step g to counting in a gamma counter, (i) subjecting normal sera utilized as a control to steps (a) to (h) and (j) comparing the counts of steps h and i.

In the above process for the detection of antibodies, ELISA techniques can be substituted for RIA techniques.

The present invention also relates to a process for predicting the outcome of hepatitis B infection which comprises carrying out an immunoassay on serum of a human to detect the presence of an antibody to an antigen coded for by the pre-S gene coded region of the envelope of hepatitis B virus employing the above-described hepatitis B peptide immunogen at regular intervals and evaluating the data.

The present invention further relates to a process for determining if a human who has been vaccinated with a vaccine against hepatitis B has become immune to hepatitis B virus. Such process involves effecting a plurality of immunoassays of serum from such human to determine if there are antibodies in the serum to an antigen coded by the pre-S gene coded region of the envelope of hepatitis B virus employing the above-described hepatitis B peptide immunogen, the immunoassays being performed on serum taken from the human at different times.

The present invention further concerns a method for detecting the presence of hepatitis B virus infection comprising effecting quantitative immunoassays on a serum sample taken from a human to determine the amount of antibodies present therein which are antibodies to an antigen coded by the pre-S gene coded region of the envelope of the hepatitis B virus employing the above-described hepatitis B peptide immunogen and comparing the value with a known standard.

The present invention further concerns a method for detecting the presence of hepatitis B virus infection comprising effecting quantitative immunoassays on a serum sample taken from a human to determine the amount of antigens coded by the pre-S gene coded region of the envelope of the hepatitis B virus employing the above-described antibodies to the hepatitis B peptide immunogen and comparing the value with a known standard.

The present invention also related to a process for raising antibodies which involves introducing into an animal the above-described hepatitis B peptide immunogen.

Still further, the present invention concerns a process for synthesizing His and Trp containing peptides which includes the steps of a. linking a first amino acid containing an alpha-amino protecting group to a resin;

b. removal of the alpha-amino protecting group;

c. coupling a second amino acid containing an alpha-amino protecting group to the first amino acid;

d. repeating steps b and c by coupling further alpha-protected amino acids to produce a desired peptide, wherein at least one of the amino acids is His and wherein at least one of said amino acids is Trp, e. cleaving the peptide from the resin and removing remaining protective groups to said first amino acids;

f. substituting a His(ImDNP) for the His;

g. substituting a Trp(InFormyl) for the Trp;

h. removing the DNP prior to the cleavage and the removing of protective groups, and i. removing the Formyl during the cleavage and the removing of protective groups.

The present invention further concerns a prophylatic method of protecting a patient against becoming infected with hepatitis B comprising administering to such patient, e.g., a human, an effective dosage of a vaccine as described hereinabove

BRIEF DESCRIPTION OF THE DRAWINGS

FIG. 2 shows amino acid sequences of the translational products of the pre-S gene region deduced from sequences of HBV DNA. The sequences are presented in one-letter amino acid code words (such code words are defined in the Definitions herein). Sequences for five distinct HBV subtypes are presented. The 6th bottom line shows amino acid residues common to all five subtypes.

FIG. 9 shows four sets of bar graphs (FIG. 9A, FIG. 9B. FIG. 9C corresponds to conjugage No. 12 and FIG. 9D corresponds to conjugate No. 19. Anti-HBs (dashed columns) and anti-S-135-155 (black columns) were assayed as described for FIG. 8.

DETAILED DESCRIPTION OF THE INVENTION

Figure 2:
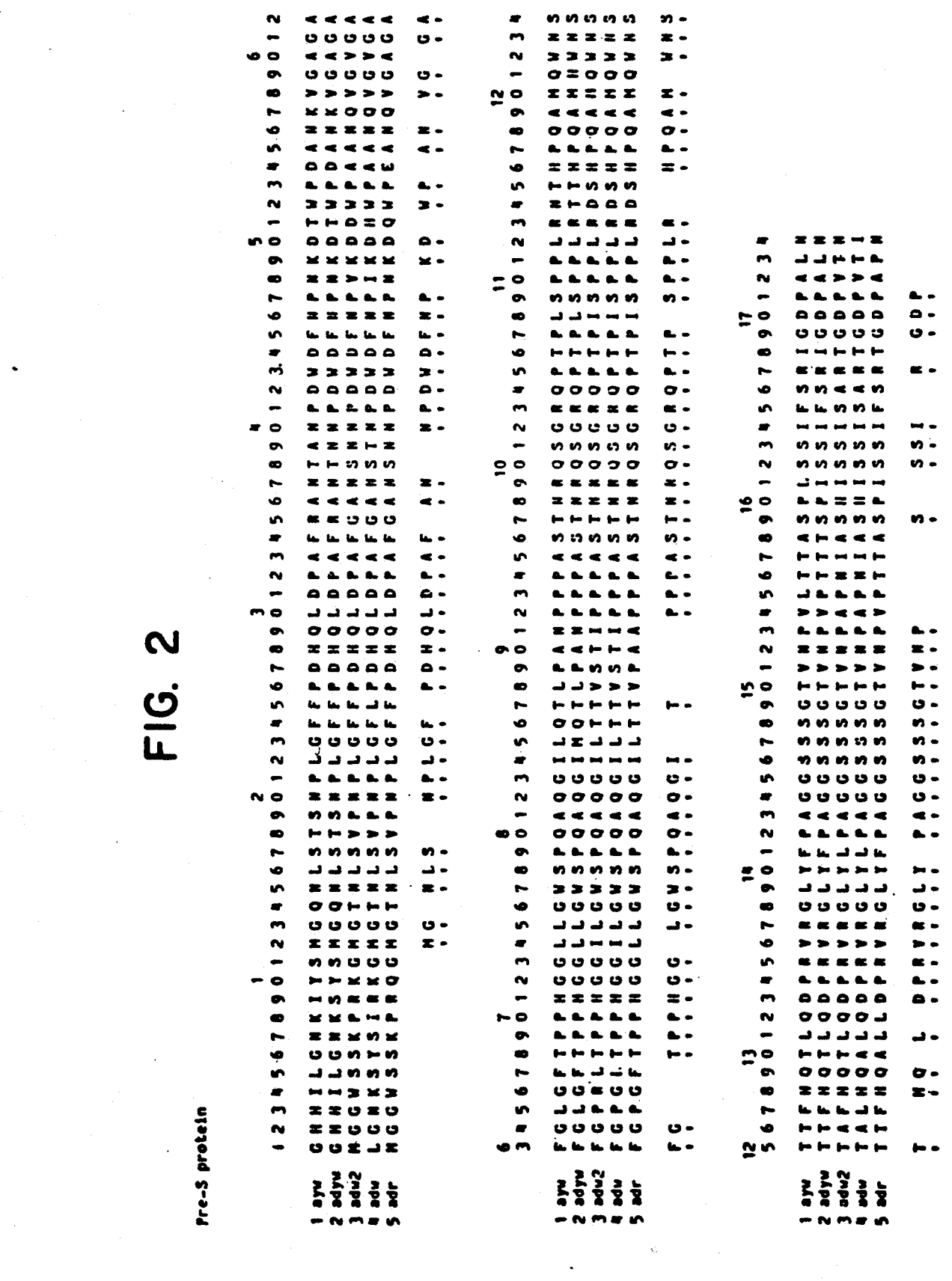
Figure 1:
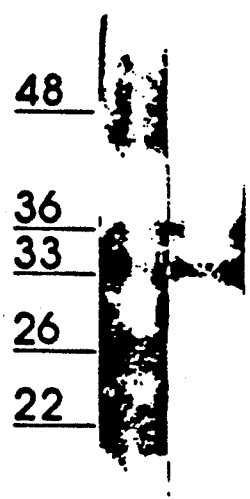
FIG. 1 is a pen and ink drawing that shows the results of submitting reduced HBsAg disassociated into its constituent polypeptides to SDS-polyacrylamide gel electrophoresis ("SDS-PAGE") in urea. Panel a shows the separated proteins detected by a silver stain and panel b is a Western blot with human antiserum to hepatitis B.

Amino acid sequences deduced from sequences of the pre-S portion of the env genes corresponding to several HBV subtypes (see FIG. 2) have the following properties distinct from those of the S-protein: (i) high hydrophilicity and high percentage of charged residues (E. Schaeffer, J. J. Sninsky, *Pro. Natl. Acad. Sci. USA,* 81, 2902 (1984)); (ii) absence of cysteine residues; (iii) the highest subtype-dependent variability among HBV DNA gene products; and (iv) little homology with analogous sequences corresponding to nonhuman hepadnaviruses (F. Galibert, T. N. Chan, E. Mandart, *J. Virol.,* 41, 51, (1982)). These properties suggest that the pre-S gene coded portion of the HBV envelope is exposed on the surface of the virion, is a target for the host's immune response and is responsible for the host range of HBV (limited to humans and some primates). Synthetic peptides and antibodies against them, having predetermined specificity offer the opportunity to explore the biological role of the pre-S protein moiety of the HBV envelope.

Cleavage of disulfide bonds within HBsAg results in:

(a) a substantial decrease of binding of polyclonal antibodies (G. N. Vyes, K. R. Rao, A. B. Ibrahim, *Science,* 178, 1300, (1972); N. Sukeno, R. Shirachi, J. Yamaguchi, N. Ishida, *J. Virol.,* 9, 182, (1972); G. R. Dreesman, F. B. Hollinger, R. M. McCombs, J. L. Melnick, *J. Gen. Virol.* 19, 129 (1973); and A. R. Neurath, N. Strick, *J. Med. Virol.,* 6, 309, (1980)) and of some monoclonal antibodies (J. Pillot, M.M. Riottot, C. Geneste, L. Phalente, R. Mangalo, *Develop. Biol. Stand.,* in press (1984)) elicited by intact HBsAg, and (b) reduction of immunogenicity (Y. Sanchez, I. Ionescu-Matiu, J. L. Melnick, G. R. Dreesman, *J. Med. Virol.* 11, 115, (1983)). However, some epitopes are resistant to reduction of disulfide bonds (M. Imai, A. Gotoh, K. Nishioka, S. Kurashina, Y. Miyakawa, M.

Mayumi, *J. Immunol.*, 112, 416, (1974)). These epitopes are common to all antigenic subtypes of HBV, but their localization on envelope components of HBV has not been determined. The present invention takes advantage of the localization of disulfide-bond independent antigenic determinants on the N-terminal portion (coded for by the pre-S gene of HBV DNA) of the minor HBsAg proteins P33 and P36, and on other regions of proteins coded for by the pre-S gene.

These determinants represent the dominant epitopes on reduced and dissociated HBsAg reacting with human anti-HBs. They are mimicked with high fidelity by pre-S. 120–145 which elicits antibodies to HBsAg about 400 times more efficiently than a synthetic peptide analogue corresponding to the S-gene (A. R. Neurath, S. B. H. Kent, and N. Strick, *Proc. Natl. Acad. Sci. USA*, 79, 7871 (1982)). No precedent exists for such high levels of virus-recognizing antibodies to a synthetic peptide analogue of an HBV protein. These antibodies could be used in a diagnostic test permitting the direct detection of the pre-S gene coded antigenic determinants in serum of HBV carriers.

The pre-S gene is the most divergent among all regions of hepadnavirus genomes (F. Galibert, T. N. Chen, E. Mandart, *J. Virol.*, 41, 51 (1982)) (HBV is a member of the hepadnavirus family).

The hepatitis B vaccine of the present invention contains a peptide, either a synthetic peptide (peptide produced by assembling individual amino acids by chemical means or by expression vectors (DNA route)) or a peptide derived from natural sources, such peptide having an amino acid chain corresponding to at least six consecutive amino acids within the pre-S gene coded region of the surface antigen of hepatitis B virus. Such chain can be, for example, at least 10, 15, 20, or 26 amino acids long. A preferred peptide according to one embodiment of the present invention is an amino acid chain disposed between sequence position pre-S 120 and pre-S 174, and more preferably such chain includes the N-terminal methionine at sequence position pre-S 120. A preferred peptide is an amino acid chain corresponding to the chain between sequence position pre-S 120 and pre-S 145, i.e., pre-S (120–145).

Preferred positions of the chain include the following: (1) The amino acid chain entirely between and including sequence position pre-S 1 and pre-S 11 for subtypes $adw_2$ and adr, (2) between and including sequence positions pre-S 10 and pre-S 40, (3) between and including sequence positions pre-S 15 and pre-S 120, (4) between and including sequence position pre-S 15 and pre-S 55, and (5) between and including sequence position pre-S 90 and pre-S 120. A particularly preferred chain according to the present invention has 26 amino acids, includes the N-terminal methionine at sequence position pre-S 120 and is disposed between sequence position pre-S 120 and pre-S 174.

Preferred peptides according to the present invention include the following:

(1) pre-S(12–32), wherein the sequence is (see FIG. 2) MGTNLSVPNPLGFFPDHQLDP for subtype $adw_2$;

(2) pre-S(120–145), wherein the sequence is (see FIG. 2) MQWNSTAFHQTLQDPRVRGLYLPAGG for subtype $adw_2$;

(3) pre-S(32–53), wherein the sequence is (see FIG. 2) PAFGANSNNPDWDFNPVKDDWP for subtype $adw_2$;

(4) pre-S(117–134), wherein the sequence is (see FIG. 2) PQAMQWNSTAFHQTLQDP for subtype $adw_2$;

(5) pre-S(94–117), wherein the sequence is (see FIG. 2) PASTNRQSGRQPTPISPPLRDSHP for subtype $adw_2$;

(6) pre-S(153–171), wherein the sequence is (see FIG. 2) PAPNIASHISSISARTGDP for subtype $adw_2$;

(7) pre-S(1–21), wherein the sequence is (see FIG. 2) MGGWSSKPRKGMGTNLSVPNP for subtype $adw_2$;

(8) pre-S(57–73), wherein the sequence is (see FIG. 2) QVGVGAFGPRLTPPHGG for subtype $adw_2$;

(9) pre-S(1–11), a. for $adw_2$, wherein the sequence is (see FIG. 2) MGGWSSKPRKG b. for adr, wherein the sequence is (see FIG. 2) MGGWSSKPRQG.

Any analogs of the pre-S gene coded sequences of the present invention involving amino acid deletions, amino acid replacements, such as replacements by other amino acids, or by isosteres (modified amino acids that bear close structural and spatial similarity to protein amino acids), amino acid additions, or isosteres additions can be utilized, so long as the sequences elicit antibodies recognizing the pre-S protein of HBV or hepatitis B surface antigen.

In the formation of a peptide derived from natural sources, a protein containing the required amino acid sequence is subjected to selective proteolysis such as by splitting the protein with chemical reagents or using enzymes. Synthetic formation of the peptide requires chemically synthesizing the required chain of amino acids.

In forming a synthetic vaccine according to the present invention, it is preferred to insure that the amino acid chain (peptide residue) corresponding to at least six consecutive amino acids within the pre-S gene coded region of hepatitis B virus has the steric configuration to be recognized by antibody to hepatitis B virus. To this end, the given chain of amino acids may have bonded thereto as part of the amino acid chain, one or more additional amino acids on either, or both sides thereof. These additional amino acids can serve as auxiliary amino acids to enhance the stabilization of the amino acid chain so that it is readily recognized by antibody to hepatitis B virus. The additional amino acids can be the same amino acids in the same sequence as they occur in the natural protein, or other amino acids may be employed.

In one form of the invention, the peptide having a chain length of minimally six amino acids can be bounded on either side thereof with additional amino acids, e.g., three amino acids on either side of the residue, to form a longer chain of amino acids. The chain of amino acids may contain more than one amino acid sequence corresponding to at least six consecutive amino acids within the pre-S region of the surface antigen of hepatitis B virus.

The length of the individual amino acid sequence would depend on the method of producing the sequence. If the sequence is made by assembling individual amino acids by chemical means, then the sequence length would generally not exceed 50 amino acids, and preferably would not exceed 40 amino acids. If the synthetic peptide is obtained from a DNA route, the chain length could be longer, for example, 100 or more amino acids. It is, however, normally shorter, and optimally considerably shorter than the natural pre-S protein. Thus, in the embodiment wherein the peptide has units of both the S region and pre-S region, its peptide portions corresponding to the S region is shorter than the natural S protein, e.g., no more than 100 amino acids, preferably no more than 40 amino acids and usually less than 30 amino acids. In such cases, the peptide portion corresponding to the pre-S region can be of a length corresponding to the entire pre-S region, but generally is less than the entire pre S region.

When the peptide contains no components corresponding to the amino acid sequence of the S region, it can contain amino acid sequences corresponding to the entire pre-S region, or shorter than the entire pre-S region.

Where, however, the amino acid sequence is part of a long chain, such as when there are more than one sequence of amino acids, the chain can contain residues of the S region of the surface antigen of hepatitis B virus, for example,

```
141 142 143 144 145 146
Lys Pro Thr Asp Gly Asn,
``` or

```
138 139 140 141 142 143 144 145 146 147 148 149
Cys Cys Thr Lys Pro Thr Asp Gly Asn Cys Thr Cys
```

Other peptides corresponding to antigenic determinants of HBsAg (S region) and thus combinable in the same chain with one or more amino acids sequences corresponding to at least six amino acids in the pre-S region of HBsAg include the following:

| | Position | Amino Acid Series |
|---|---|---|
| (1) | | Ser—Thr—Gly—Pro—Ser (117) ... (121)—Lys(122)—Thr—Cys(124)=Cys(137)—Met—Thr—Ala—Gly—Thr—Ser—Met—Tyr—Pro—Ser (cyclic structure) |
| (2) | 48-81 | Cys—Leu—Gly—Gln—Asn—Ser—Gln—Ser—Pro—Thr—Ser—Asn—His—Ser—Pro—Thr—Ser—Cys—Pro—Pro—Thr—Cys—Pro—Gly—Thr—Arg—Trp—Met—Cys—Leu—Arg—Arg—Phe—Ile |
| (3) | 2-16 | Glu—Asn—Ile—Thr—Ser—Gly—Phe—Leu—Gly—Pro—Leu—Leu—Val—Leu—Gln—Cys |
| (4) | 22-35 | Leu—Thr—Arg—Ile—Leu—Thr—Ile—Pro—Gln—Ser—Leu—Asp—Ser—Trp—Cys |
| (5) | 38-52 | Ser—Leu—Asn—Phe—Leu—Gly—Gly—Thr—Thr—Val—Cys—Leu—Gly—Gln—Asn |
| (6) | 47-52 | Val—Cys—Leu—Gly—Gln—Asn |
| (7) | 95-109 | Leu—Val—Leu—Leu—Asp—Tyr—Gln—Gly—Met—Leu—Pro—Val—Cys—Pro—Leu |
| (8) | 104-109 | Leu—Pro—Val—Cys—Pro—Leu | various moieties, for example, segments of polyamino acids or polysaccharides.

In addition to containing one or more different or the same sequences of amino acids corresponding to at least six consecutive amino acids within the pre-S region of hepatitis B virus, e.g., containing more than one sequence of amino acids corresponding to different epitopes (antigenic determinants) in the pre-S region of hepatitis B virus, the vaccine of the present invention can contain amino acid chains containing epitopes of different antigens or allergens so as to form a vaccine directed to hepatitis B virus and to one or more additional diseases, e.g., measles, influenza, smallpox, polio, diptheria, just to name a few. Such additional amino acid sequences can be of varying amino acid chain lengths.

A hepatitis B vaccine according to the present invention can include in addition to one or more amino acid sequences corresponding to at least six consecutive amino acids within the pre-S region of the surface antigen of hepatitis B virus, one or more amino acid sequences corresponding to consecutive amino acids within the S region of the surface antigen of hepatitis B virus, for example, The sequences of amino acids can be interconnected with one another such as by cross-linking or by being bonded directly thereto in the form of a branched chain, or the respective sequences can be bonded to a central "carrier".

There is realized by the present invention a synthetic vaccine which is characterized by the absence of naturally occuring envelope proteins of hepatitis B virus, i.e., the vaccine of the present invention is composed of one or more peptide sequences corresponding to a limited portion of the hepatitis B virus envelope protein. The vaccine of the present invention is also free of other proteins found in the virion. Vaccines can be synthesized which are free of biologically produced components, free of viral components whether they be active or inactive, free of antibodies, free of deoxyribonucleic acid (DNA), and are therefore likely to be substantially free from undesirable side effects commonly found with other vaccines (e.g., unintentional infection with virus, allergic reactions, fevers, etc.).

It should be understood that the vaccine of the present invention can be in admixture with other proteins and these proteins include the proteins of known antigens or allergens. Thus when it is stated herein that the vaccine is characterized by the absence of an amino acid sequence corresponding to the naturally occurring envelope proteins of the hepatitis B virus it is meant that notwithstanding the absence of such proteins, the composition functions as a vaccine, i.e., provides protective immunization by formation of antibodies.

The peptide of the present invention is such that it is capable of forming "neutralizing antibodies", i.e., antibodies that will protect patients against hepatitis B virus. Accordingly, the present invention is also directed to methods for protecting a patient against contracting hepatitis B.

The peptides and vaccines of the present invention can be used to improve immune response and to overcome non-responsiveness to certain known hepatitis B virus vaccines (e.g., containing no peptides corresponding to amino acid sequences in the pre-S region).

The peptides of the present invention can be utilized in conjunction with peptides containing amino acid chains corresponding to consecutive amino acids within the S gene coded region of HBsAg. Also, embodied by the present invention is a peptide containing amino acids corresponding to consecutive amino acids spanning both the pre-S and S region, e.g., pre-S 160 to S 20.

A carrier may be provided for the synthetic peptide of the invention. It should be understood, however, that a carrier may not be required to practice the present invention, i.e., a carrier may not be required to produce antibodies according to the present invention.

The "carrier" is simply a physiologically acceptable mass to which the synthetic peptide is attached and which is expected to enhance the immune response. A carrier can comprise simply a chain of amino acids or other moieties and to that end it is specifically contemplated to use as a carrier a dimer, oligomer, or higher molecular weight polymer of a sequence of amino acids defining a synthetic peptide of the invention. In other words, having determined the desired sequence of amino acids to form the synthetic peptide, these amino acids can be formed from naturally available materials or synthetically and can be polymerized to build up a chain of two or more repeating units so that repeating sequences serve both as "carrier" and synthetic peptide. Stated differently, an independent carrier may not be required. Alternatively, additional amino acids can be added to one or both ends of the amino acid chain that defines the synthetic peptide. It is preferred that alternative carriers comprise some substance, animal, vegetable or mineral, which is physiologically acceptable and functions to present the synthetic peptide so that it is recognized by the immune system of a host and stimulates a satisfactory immunological response. Thus, a wide variety of carriers are contemplated, and these include materials which are inert, which have biological activity and/or promote an immunological response. For instance, proteins can be used as carriers. Examples of protein carriers include tetanus toxoid, keyhole lympet hemocyanin, etc.

Polysaccharides are also contemplated as carriers, and these include especially those of molecular weight 10,000 to 1,000,000, including, in particular, starches, dextran, agarose, ficoll or its carboxy methyl derivative and carboxy methyl cellulose.

Polyamino acids are also contemplated for use as carriers, and these polyamino acids include, among others, polylysine, polyalanyl polylysine, polyglutamic acid, polyaspartic acid and poly ($C_2$-$C_{10}$) amino acids.

Organic polymers can be used as carriers, and these polymers include, for example, polymers and copolymers of amines, amides, olefins, vinyls, esters, acetals, polyamides, carbonates and ethers and the like. Generally speaking, the molecular weight of these polymers will vary dramatically. The polymers can have from two repeating units up to several thousand, e.g., two thousand repeating units. Of course, the number of repeating units will be consistent with the use of the vaccine in a host animal. Generally speaking, such polymers will have a lower molecular weight, say between 10,000 and 100,000 (the molecular weight being determined by ultracentrifugation).

Inorganic polymers can also be employed. These inorganic polymers can be inorganic polymers containing organic moieties. In particular, silicates and aluminum hydroxide can be used as carriers. It is preferred that the carrier be one which is an immunological adjuvant. In such cases, it is particularly contemplated that the adjuvant be muramyl dipeptide or its analogs.

The carrier can also be the residue of a crosslinking agent employed to interconnect a plurality of synthetic peptide containing chains. Crosslinking agents which have as their functional group an aldehyde (such as glutaraldehyde), carboxyl, amine, amido, imido or azidophenyl group. In particular, there is contemplated the use of butyraldehyde as a crosslinking agent, a divalent imido ester or a carbodiimide. Particularly contemplated divalent imido esters are those of the formula

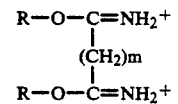

wherein m is 1 to 13 and R is an alkyl group of 1 to 4 carbon atoms. Particularly contemplated carbodiimides for use as crosslinking agents include cyclohexylcarboxiimide, ethyldimethylaminopropyl carbodiimide, N-ethylmorpholino cyclohexyl carbodiimide and diisopropyl carbodiimide.

Chemical synthesis of peptides is described in the following publications: S. B. H. Kent, *Biomedical Polymers*, eds. Goldberg, E. P. and Nakajima, A. (Academic Press, New York), 213-242, (1980); A. R. Mitchell, S. B. H. Kent, M. Engelhard, and R. B. Merrifield, *J. Org. Chem.*, 43, 2845-2852, (1978); J. P. Tam, T. -W. Wong, M. Riemen, F. -S. Tjoeng, and R. B. Merrifield, *Tet. Letters*, 4033-4036, (1979); S. Mojsov, A. R. Mitchell, and R. B. Merrifield, *J. Org. Chem.*, 45, 555-560, (1980); J. P. Tam, R. D. DiMarchi and R. B. Merrifield, *Tet. Letters*, 2851-2854, (1981); and S. B. H. Kent, M. Riemen, M. Le Doux and R. B. Merrifield, *Proceedings of the IV International Symposium on Methods of Protein Sequence Analysis*, (Brookhaven Press, Brookhaven, N.Y.), in press, 1981.

Chemical Synthesis: In the so-called "Merrifield solid phase procedure" the appropriate sequence of L-amino acids is built up from the carboxyl terminal amino acid to the amino terminal amino acid. Starting with the appropriate carboxyl terminal amino acid attached to a polystyrene (or other appropriate) resin via chemical linkage to a chloromethyl group, benzhydrylamine group, or other reactive group of the resin, amino acids are added one by one using the following procedure. The peptide-resin is:

(a) washed with methylene chloride;
(b) neutralized by mixing for 10 minutes at room temperature with 5% (v/v) diisopropylethylamine (or other hindered base) in methylene chloride;
(c) washed with methylene chloride;
(d) an amount of amino acid equal to six times the molar amount of the growing peptide chain is activated by combining it with one-half as many moles of a carbodiimide (e.g., dicyclohexylcarbodiimide, or diisopropylcarbodiimide) for ten minutes at 0° C., to form the symmetric anhydride of the amino acid. The amino acid used should be provided originally as the N-alpha-tert.butyloxycarbonyl derivative, with side chains protected with benzyl esters (e.g. aspartic or glutamic acids), benzyl ethers (e.g., serine, threonine, cysteine or tyrosine), benzyloxycarbonyl groups (e.g., lysine) or other protecting groups commonly used in peptide synthesis.
(e) the activated amino acid is reacted with the peptide-resin for two hours at room temperature, resulting in addition of the new amino acid to the end of the growing peptide chain.
(f) the peptide-resin is washed with methylene chloride;
(g) the N-alpha-(tert. butyloxycarbonyl) group is removed from the most recently added amino acid by reacting with 30 to 65%, preferably 50% (v/v) trifluoroacetic acid in methylene chloride for 10 to 30 minutes at room temperature;
(h) the peptide-resin is washed with methylene chloride;
(i) steps (a) through (h) are repeated until the required peptide sequence has been constructed.

The peptide is then removed from the resin and simultaneously the side-chain protecting groups are removed, by reaction with anhydrous hydrofluoric acid containing 10% v/v of anisole or other suitable (aromatic) scavenger. Subsequently, the peptide can be purified by gel filtration, ion exchange, high pressure liquid chromatography, or other suitable means.

In some cases, chemical synthesis can be carried out without the solid phase resin, in which case the synthetic reactions are performed entirely in solution. The reactions are similar and well known in the art, and the final product is essentially identical.

Isolation from natural sources: If sufficient quantities of the whole protein antigen are available, a limited portion of the molecule, bearing the desired sequence of amino acids may be excised by any of the following procedures:

(a) Digestion of the protein by proteolytic enzymes, especially those enzymes whose substrate specificity results in cleavage of the protein at sites immediately adjacent to the desired sequence of amino acids;
(b) Cleavage of the protein by chemical means. Particular bonds between amino acids can be cleaved by reaction with specific reagents. Examples include: bonds involving methionine are cleaved by cyanogen bromide; asparaginyl-glycine bonds are cleaved by hydroxylamine;
(c) A combination of proteolytic and chemical cleavages.

It should also be possible to clone a small portion of the DNA, either from natural sources or prepared by synthetic procedures, or by methods involving a combination thereof, that codes for the desired sequence of amino acids, resulting in the production of the peptide by bacteria, or other cells.

Analogously, one can form chains containing a plurality of amino acid sequences by the following technique: An aqueous solution of a peptide or peptides is mixed with a water-soluble carbodiimide (e.g., ethyldimethyl-aminopropylcarbodiimide). This results in polymerization of the peptide(s); depending on the use of the side chain blocking groups mentioned above, either straight chain or branched polymers of the peptide can be made.

If desired the synthetic peptide of the present invention can have bonded thereto a chain of any of the following moieties: polypeptide, polyamino acid, polysaccharide, polyamide or polyacrylamide which can serve as a stabilizing chain or as a bridge between amino acids of the individual chains. Such chains are available commercially or, in the case of polyamino acids, are formed by a process which comprises: mixing a solution of the desired amino acid sequence with a solution of the N-carboxylanhydride of the amino acid and allowing a base-catalyzed polymerization to occur, which is initiated by the amine groups of the peptide.

Although a carrier may not be required, if a carrier is employed the deposition of a chain or chains on a "carrier" can be effected as follows:

1. Protein Carrier: The protein and the synthetic peptide are dissolved together in water or other suitable solvent, and covalently linked via amide bonds formed through the action of a carbodiimide. The resulting product may contain one or more copies of the peptide per protein monomer. Alternatively, the reduced peptide may be added to a carrier containing sulfhydryl groups to form disulfide bonds. Yet another method involves the addition of reduced peptide to protein carriers containing maleimidyl groups to form a covalent linkage by a Michael addition, or any other covalent attachment means.

2. Polysaccharide Carriers: Oligosaccharide carriers should have molecular weights in the range 1,000 to 1,000,000. In order to covalently link these to synthetic peptides, suitable functional groups must first be attached to them. Carboxyl groups may be introduced by reacting with iodoacetic acid to yield carboxymethylated polysaccharides, or by reacting with carbonyldiimidazole to yield activated carbonyl esters. Carboxymethyl polysaccharides are coupled to the peptide by a carbodimide reaction, while the activated carbonyl esters react spontaneously with peptides. Multiple copies of the synthetic peptide should be attached to each oligosaccharide unit.

3. Polyamino Acid Carriers: These carriers should have molecular weights in the range 1,000 to 1,000,000. Polylysine and polyornithine have primary amino groups on their side chains; polyaspartic acid and polyglutamic acid have carboxyl groups. Peptides may be coupled to these via amide bonds using the carbodiimide reaction. Another carrier that provides amino groups for coupling is polylysine to which polyalanine can be attached to the side chains of the lysine residues. The synthetic peptide may be attached to the ends of polyalanine chains, also by a carbodiimide reaction. Multiple copies of the synthetic peptide should be attached to each oligopeptide unit.

The novel carrier of the present invention includes a lipid vesicle having active sites on the outer surface thereof. Such active sites include —COOH, —CHO, —NH$_2$ and —SH. The lipid carrier can be stabilized by cross-linking by a stabilizing agent such as an aldehyde having at least two functional groups, such as a bifunctional aldehyde, e.g., glutaraldehyde.

The bonding of the peptide to the lipid vesicle carrier occurs at the active sites on the lipid vesicle on the exterior surface of the carrier. Without wishing to be bound by any theory of operability, it is believed that such bonding is at least covalent bonding.

It is possible to bind a peptide to two active sites on the outer surface of the lipid vesicle. For example, a —NH$_2$ group at one end of a peptide can bind with a —COOH active site on the outer surface of the lipid vesicle. The other end of the peptide can then bind with another active site on the lipid vesicle, for example, a —COOH group on the other end of the peptide can bind with a —NH$_2$ active site on the lipid vesicle.

The preferred carrier to support the synthetic peptides of the present invention is a lipid vesicle. Lipid vesicles can be formed by sonicating a lipid in an aqueous medium, by resuspension of dried lipid layers in a buffer or by dialysis of lipids dissolved in an organic solvent against a buffer of choice. The latter procedure is preferred. Lipid vesicles consist of spheres of lipid bilayers that enclose part of the aqueous medium.

Lipid vesicle (non-protein) carriers according to the present invention can be produced in a variety of ways. The preferred method to produce such carriers would be to treat a lipid vesicle containing aminoalkanes and diaminoalkanes having 10 to 18 carbon atoms, for example stearylamine, cetylamine and myrististylamine with a polyaldehyde, such as a dialdehyde, for example, butanedial (succinaldehyde), pentanedial (glutaraldehyde), hexanedial (adipoldehyde), heptanedial (pimelicaldehyde) and octanedial (suberaldehyde). Alternatively, a liposome containing aminoalkenes and diaminoalkenes having 10 to 18 carbon atoms, for example, oleylamine, can be treated with the aforementioned polyaldehydes. The lipid vesicle carrier thus formed has active aldehyde groups on the surface thereof allowing the direct linking of peptides via their N-terminal or lysine groups.

Peptides linked to lipid vesicle carriers according to the present invention can also be prepared by treating an amino containing lipid vesicle as described above with a peptide activated by carbodiimide, for example, N-ethyl-N' (dimethylaminopropyl) carbodiimide.

Alternatively a carbodiimide activated peptide is linked to polyaldehyde, e.g., dialdehyde, treated lipid vesicles which have been further derivatized by reaction with a water-soluble diaminoalkane, e.g., ethylene diamine and propylene diamine.

Still further, lipid vesicles containing fatty acids (saturated and unsaturated) having 12 to 18 carbon atoms, e.g., stearic acid, oleic acid, palmitic acid and myristic acid, are activated with carbodiimide. Thereafter, the activated lipid vesicle is reacted with a peptide.

Another approach to form a carrier according to the present invention involves using a fatty acid aldehyde as a component of the lipid vesicle and treating such lipid vesicle as described for glutaraldehyde treated lipid vesicles. Such lipid vesicle reacts directly with amino groups of peptides.

In a preferred embodiment of a carrier according to the present invention, the aforementioned lipid vesicle carrier formed by treating a amino or diaminoalkane (or amino or diaminoalkene) having 10 to 18 carbon atoms with a polyaldehyde is further reacted with cysteine (L-or D- or LD- cysteine). These lipid vesicles are then reacted with a peptide having —SH groups, i.e., cysteine containing peptides. The link between the lipid vesicle and the peptide is mediated by a disulfide bond.

Alternatively, a fatty acid mercaptan is used as a component of the lipid vesicle, for example, octadecanethiol. A cysteine containing peptide is directly linked to such lipid vesicle.

Another approach to form carriers according to the present invention involves the preparation of the above described fatty acid mercaptan containing lipid vesicles which are further reacted with a dimaleimide, for example, para or ortho N-N'-phenylenedimaleimide. Such lipid vesicle is then reacted with a cysteine containing peptide.

Alternatively, the link between the appropriate lipid vesicle and the appropriate peptide can be accomplished by commercially available cross-linking reagents such as dimethyl adipimidate; dimethyl 3,3'-dithiobis-propionimidate; 2-iminothiolane; di-succinimidyl suberate; bis[2-(succinimidooxy carbonyloxy)-ethyl] sulfone; disuccinimidyl tartarate; dithiobis (succinimidyl propionate); ethylene glycol bis(succinimidyl succinate); N-5-azido-2-nitrobenzoyloxysuccinimide; p-azidophenacyl bromide; p-azido-phenylglyoxal; 4-fluoro-3-nitrophenyl azide; N-hydroxysuccinimidyl-4-azidebenzoate; N-hydroxysuccinimidyl-4-azidosalicylic acid; m-maleimidobenzoyl N-hydroxy succinimide ester; methyl-4-azidobenzoimidate; p-nitrophenyl 2-diazo-3,3,3-trifluoroproprionate; N-succinimidyl-6 (4'-azido-2'-nitrophenylamino) hexanoate; succinimidyl 4-(N-maleimidomethyl) cyclohexane-1-carboxylate; succinimidyl 4-(p-maleimidomethyl) butyrate; N-(4-azidophenylthio)phthalimide; ethyl 4-aziodophenyl 1, 4-dithiobutyrimidate; N-succinimidyl (4-azidophenyldithio) propionate; 1-5-difluoro-2, 4-dinitrobenzene; 4,4'-difluoro-3,3'-dinitrodiphenyl-sulfone; 4,4'-diisothiocyano-2,2'-disulfonic acid stilbene; p-phenylenediisothiocyanate; 4,4'-dithiobisphenylazide; erythritolbiscarbonate; N-succinimidyl 3-(2-pyridyldithiol) propionate; dimethyl pimelimidate and dimethyl suberimidate.

The lipid vesicles according to the present invention act not only as carriers, but also as adjuvants.

The lipid vesicle synthetic carriers of the present invention can be utilized to bind synthetic peptide analogues (eliciting protective antibodies) of various viral, bacterial, allergen and parasitic proteins of man and animals, besides synthetic peptide analogues of hepatitis B surface antigen, and especially the novel synthetic peptide analogue of hepatitis B surface antigen containing amino acid sequences corresponding to amino acid sequences in pre-S gene coded region of the HBV.

Accordingly, the lipid vesicle synthetic carriers of the present invention can be used to bind with synthetic peptide analogues of the following viruses: influenza hemagglutinin (A/memphis/102/72 strain, A/Eng 1878/69 strain, A/NT/60/68/29c strain, and A/Qu/7/70 strain), fowl plague virus hemagglutinin, vaccinia, polio, rubella, cytomegalovirus, small pox, herpes simplex types I and II, yellow fever, Infectious ectromelia virus, Cowpox virus, Infectious bovine rhinotracheitis virus, Equine rhinopneumonitis (equine abortion) virus, Malignant catarrh virus of cattle, Feline rhinotracheitis virus, Canine herpes virus, Epstein-Barr virus (associated with infectious mononucleosis and Burkitt lymphoma), Marek's disease virus, Sheep pulmonary adenomatosis (Jaagziekte) virus, Cytomegaloviruses, Adenovirus group, Human papilloma virus, Feline panleucopaenia virus, Mink enteritis virus, African horse sickness virus (9 serotypes), Blue tongue virus (12 serotypes), Infectious pancreatic necrosis virus of trout, Fowl sarcoma virus (various strains), Avian leukosis virus (visceral, erythroblastic and myeloblastic), Osteopetrosis virus, Newcastle disease virus, Parainfluenza virus 1, Parainfluenza virus 2, Parainfluenza virus 3, Parainfluenza 4, Mumps virus, Turkey virus, CANADA/58, Canine distemper virus, Measles virus, Respiratory syncytial virus, Myxovirus, Type A viruses such as Human influenza viruses, e.g., Ao/PR8/34, A1/-CAM/46, and A2/Singapore/1/57; Fowl plaque virus; Type B influenza viruses, e.g., B/Lee/40; Rabies virus; Eastern equinine encephalitis virus; Venezuelan equine encephalitis virus; Western equine encephalitis virus; Yellow fever virus, Dengue type 1 virus (=type 6), Dengue type 2 virus (=type 5); Dengue type 3 virus; Dengue type 4 virus; Japanese encephalitis virus, Kyasanur Forest virus; Louping ill virus; Murray Valley encephalitis virus; Omsk haemorrhagic fever virus (types I and II); St. Louis encephalitis virus; Human rhinoviruses, Foot-and-mouth disease virus; Poliovirus type 1; Enterovirus Polio 2; Enterovirus Polio 3; Avian infectious bronchitis virus; Human respiratory virus; Transmissible gastro-enteritis virus of swine; Lymphocytic choriomeningitis virus; Lassa virus; Machupo virus; Pichinde virus; Tacaribe virus; Papillomavirus; Simian virus; Sindbis virus, and the like.

The lipid vesicle synthetic carriers of the present invention can be used to bind synthetic peptide analogues of bacteria, for example, leprosy, tuberculosis, syphilis and gonorrhea.

The lipid vesicle synthetic carriers of the present invention can also be used to bind synthetic peptide analogues of the following parasites: organisms carrying malaria (P. Falciparum, P. Ovace, etc.), Schistosomiasis, Onchocerca Volvulus and other filiarial parasites, Trypanosomes, Leishmania, Chagas disease, amoebiasis, hookworm, and the like.

The lipid vesicle carriers of the present invention can be used to bind the novel peptides of the present invention corresponding to amino acid sequences in the pre-S region of HBsAg. The lipid vesicle carriers of the present invention can also be used to bind amino acid sequences in the S region, as well as other amino acid sequences for other virus, etc.

Amino acid sequences (corresponding to amino acids in the S region) which contains an antigenic determinant for hepatitis B surface antigen can be linked to the lipid vesicle carrier of the present invention. T. P. Hopp, "A Synthetic Peptide with Hepatitis B Surface Antigen Reactivity", Mol. Imm., 18, 9, 869–872, 1981, propose the following sequence corresponding to the S region of HBsAg:

| 138 | 139 | 140 | 141 | 142 | 143 | 144 | 145 | 146 | 147 | 148 | 149 |
|---|---|---|---|---|---|---|---|---|---|---|---|
| Cys | Cys | Thr | Lys | Pro | Thr | Asp | Gly | Asn | Cys | Thr | Cys |

Other peptides mimicking the antigenic determinant of HBsAg (S region) include the following:

(1) Peptide 1

```
      X
       \
        Lys
        122
         |
        Thr
         |
  Ser — Cys=Cys — Met — Thr
   |   137  124           |
  Pro                    Thr
   |                      |
  Tyr                    Ala
   |                      |
  Met — Ser — Thr — Gly — Gln
```

Peptide 2 contains 5 additional amino acid residues:

Ser—Thr—Gly—Pro—Ser—X,
117                        121

G. R. Dreesman, Y. Sanchez, I. Ionescu-Matiu, J. T. Sparrow, H. R. Six, D. L. Peterson, F. B. Hollinger and J. L. Melnick, "Antibody to Hepatitis B Surface Antigen After A Single Inoculation of Uncoupled Synthetic HBsAg Peptides", Nature, 295, 158–160, 1982; and (2) the following peptides:

| POSITION | SEQUENCE |
|---|---|
| 48–81 | Cys-Leu-Gly-Gln-Asn-Ser-Gln-Ser-Pro-Thr-Ser-Asn-His-Ser-Pro-Thr-Ser-Cys-Pro-Pro-Thr-Cys-Pro-Gly-Tyr-Arg-Trp-Met-Cys-Leu-Arg-Arg-Phe-Ile |
| 2–16 | Glu-Asn-Ile-Thr-Ser-Gly-Phe-Leu-Gly-Pro-Leu-Leu-Val-Leu-Gln-Cys |
| 22–35 | Leu-Thr-Arg-Ile-Leu-Thr-Ile-Pro-Gln-Ser-Leu-Asp-Ser-Trp-Cys |
| 38–52 | Ser-Leu-Asn-Phe-Leu-Gly-Gly-Thr-Thr-Val-Cys-Leu-Gly-Gln-Asn |
| 47–52 | Val-Cys-Leu-Gly-Gln-Asn |
| 95–109 | Leu-Val-Leu-Leu-Asp-Tyr-Gln-Gly-Met-Leu-Pro-Val-Cys-Pro-Leu |
| 104–109 | Leu-Pro-Val-Cys-Pro-Leu |

R. Arnon, "Anti-influenza Response Achieved by Immunization With A Synthetic Conjugate", Proc. Natl. Acad. Sci. USA, 79, 569–573, 1982. The peptide corresponds to the sequence serine-91 to leucine-108 of the amino acid chain of the virus.

A peptide containing an amino acid sequence mimicking the antigenic determinant of polyoma virus medium size tumor antigen is Lys-Arg-Ser-Ars-His-Phe, G. Walter, M. A. Hutchinson, T. Hunter and W. Eckhart, "Purification of Polyoma Virus Medium-Size Tumor Antigen by Immunoaffinity Chromatography", Proc. Natl. Acad. Sci USA, 79, 4025–4029, 1982.

A peptide containing an amino acid sequence mimicking the antigenic determinant of poliovirus replicase antigen is as follows:

Tyr—Ser—Thr—Leu—Tyr—Arg—Arg—Trp—Leu—Asp—Ser—Phe,
450                                                                          461

M. H. Baron and D. Baltimore, "Antibodies Against a Synthetic Peptide of the Poliovirus Replicase Protein: Reaction with Native, Virus-Encoded Proteins and Inhibition of Virus-Specific Polymerase Activities In Vitro". Jour. Virology, 43, 3969–3978, 1982.

Peptides containing an amino acid sequence mimicking the antigenic determinant of simian virus 40 large tumor antigen are as follows:

Met—Asp—Lys—Val—Leu—Asn—Arg and
Lys—Pro—Pro—Thr—Pro—Pro—Pro—Glu—Pro—Glu—Thr,

G. Walter, K. H. Scheidtmann, A. Carbone, A. P. Laudano and R. A. Lerner, N. Green, H. Alexander, F. -T. Liu, J. G. Sutcliffe and T. M. Shinnick, "Chemically Synthesized Peptides Predicted From the Nucleotide Sequence of the Hepatitis B Virus Genome Elicit Antibodies Reactive With the Native Envelope Protein of Dane Particles", Proc. Natl. Acad. Sci. USA, 78, 6, 3403-3407, 1981.

A peptide containing an amino acid sequence mimicking the antigenic determinant of retrovirus R antigen is as follows:

Leu—Thr—Gln—Gln—Phe—His—Gln—Leu—Lys—Pro
Ile—Glu—Cys—Glu—Pro,

J. G. Sutcliffe, T. M. Shinnick, N. Green, F. -T. Liu, H. L. Niman and R. A. Lerner, "Chemical Synthesis of A Polypeptide Predicted From Nucleotide Sequence Allows Detection Of A New Retroviral Gene Product", Nature, 287, 1980.

A peptide containing an amino acid sequence mimicking the antigenic determinant of avian sarcoma virus antigen is as follows:

Glu—Asp—Asn—Glu—Tyr—Thr—Ala—Arg—Gln—Gly,

T. W. Wong and Alan R. Goldberg, "Synthetic Peptide Fragment Of src Gene Product Inhibits the src Protein Kinase and Cross reacts Immunologically With Avian onc Kinases and Cellular Phosphoproteins", Proc. Natl. Acad. USA, 78, 12, 7412-7416, 1981.

Peptides containing an amino acid sequence mimicking the antigenic determinant of foot-and-mouth disease virus antigen are as follows:

141
Val Pro Asn Leu Arg Gly Asp Leu Gly Val

160
Leu Ala Gly Lys Val Ala Arg Thr Leu Pro and

201
His Lys Gln Lys Ile Val Ala Pro Val Lys Gln Thr Leu,

J. L. Bittle, R. A. Houghten, H. Alexander, T. M. Shinnick, J. G. Sutcliffe, R. A. Lerner, D. J. Rowlands and F. Brown, "Protection Against Foot-And-Mouth Disease By Immunization With A Chemically Synthesized Peptide Predicted From the Viral Nucleotide Sequence", Nature, 298, 30-33, 1982.

A peptide containing an amino acid sequence mimicking the antigenic determinant of hemagglutinin X-31 (H3N2) influenza virus antigen is as follows:

123    125
Glu—Gly—Phe—Thr—Trp—Thr—Gly—

130                    135
Val—Thr—Gln—Asn—Gly—Gly—Ser—

-continued
140
Asp—Ala—Cys—Lys—Arg—Gly—Pro—

145                    150
Gly—Ser—Gly—Phe—Phe—Ser—Arg—

151
Leu,

D. C. Jackson, J. M. Murray, D. O. White, C. N. Fagan and G. W. Tregear, "Antigenic Activity of a Synthetic Peptide Comprising the 'Loop' Region of Influenza Virus Hemagglutinin", Virology, 120, 273-276, 1982.

A peptide containing an amino acid sequence mimicking the antigenic determinant of hemagglutinin of type A H3N2 influenza virus antigen was synthesized by G. M. Muller, M. Shapira and R. F. Doolittle, "Antibodies Specific for the Carboxy- And Amino-Terminal Regions of Simian Virus 40 Large Tumor Antigen", Proc. Natl. Acad. Sci USA, 77, 9, 5179-5200, 1980.

A peptide containing an amino acid sequence mimicking the antigenic determinant of influenza virus strain 3QB antigen is $Ile_1 Val_1 Asx_2 Thr_1 Ser_2 Glx_2 Pro_1 Gly_3 Ala_1 Leu_1 Lys_1$, A. Aitken and C. Hannoun, "Purification of Haemagglutinin and Neuraminidase from Influenza Virus Strain 3QB and Isolation of a Peptide From an Antigenic Region of Haemagluttinin", Eur. J. Biochem, 107, 51-56, 1980.

Peptides containing an amino acid sequence mimicking the antigenic determinant of diptheria antigen are given as follows:

Natural DT Loop
—Cys—Ala—Gly—Asn—Arg—Val—Arg—Arg—Ser—Val—
186                   190                   195

Gly—Ser—Ser—Leu—Lys—Cys—
                           201

Synthetic Peptide
Tetradecapeptide           Gly(188)---Cys-(201)
Hexadecapeptide            Cys(186)---Cys-(201)
Octadecapeptide            Ala—Ala—Cys(186)---Cys-(201)

F. Audibert, M. Jolivet, L. Chedid, R. Arnon and M. Sela, "Successful Immunization With a Totally Synthetic Diphtheria Vaccine", Proc. Natl. Acad. Sci. USA, 79, 5042-5046, 1982.

A peptide containing an amino acid sequence mimicking the antigenic determinant of Streptococcus pyogenes M antigen is as follows:

5
Asn—Phe—Ser—Thr—Ala—Asp—Ser—Ala—Lys 10                    15
Ile—Lys—Thr—Leu—Glu—Ala—Glu—Lys—Ala—Ala—

20                    25
Leu—Ala—Ala—Arg—Lys—Ala—Asp—Leu—Glu—Lys—

30                    35
Ala—Leu—Glu—Gly—Ala—Met

E. H. Beachey, J. M. Seyer, D. B. Dale, W. A. Simpson and A. H. Kang, "Type-Specific Protective Immunity Evoked by Synthetic Peptide of Streptococcus Pyogenes M Protein", Nature, 292, 457-459, 1981.

The lipid vesicle carrier of the present invention can thus be utilized to bind with any amino acid sequence which includes the antigenic determinant for a specific antigen.

The lipid vesicle carriers of the present invention can also be used to bind with enzymes.

The present invention is also directed to diagnostic tests for direct detection of HBV antigens and HBV antibodies.

In order to detect HBV antigens containing proteins coded for by the pre-S gene in sera of HBV-infected animals such as humans, radioimmunoassay (RIA) or enzyme-linked immunosorbent assay (ELISA) can be employed.

One test for detecting HBV antigens according to the present invention is as follows:

(1) a solid substrate containing binding sites thereon, e.g., polystyrene beads, is coated with antibodies to a peptide having an amino acid chain corresponding to at least six amino acids within the pre-S gene coded region of the envelope of HBV, the peptide free of an amino acid sequence corresponding to the naturally occuring proteins of HBV;

(2) the coated beads are then washed with, for example, tris buffered saline, to remove excess antibody;

(3) the beads are then contacted with a protein-containing solution, such as bovine serum albumin (BSA) or gelatin to saturate protein binding sites on the beads (to prevent or reduce non-specific binding)-a convenient concentration of such protein-containing solution can be employed such as 1 mg/ml to 50 mg/ml;

(4) beads are then washed to remove excess BSA or gelatin;

(5) the beads are then incubated with samples suspected to contain HBV or HBsAg (normal sera is utilized as a control);

(6) the beads are then washed with a solution, e.g., tris buffered saline solution, and mixed with a radiolabeled antibody, e.g., $I^{125}$ labeled antibody (antibody to either the peptide or to HBsAg);

(7) the beads are then incubated;

(8) the beads are then washed and counted in a gamma counter.

If the specimens have counts at least 2.1 times higher than counts of the control, then the specimens are positive.

The pre-S gene coded peptides according to the present invention can be employed as a diagnostic tool to detect antibodies to the pre-S region of HBV in a given sample. The pre-S gene coded peptide, for example, pre-S (120-145), pre-S (12-32), pre-S (32-53), or pre-S (117-134), pre-S(1-21), pre-S(94-117), pre-S(153-171), pre-S(32-53) and pre-S(57-73), is adsorbed on a solid substrate, containing binding sites thereon for example, polystyrene beads. The substrate is thereafter contacted with a substance (protein containing solution), for example, gelatin BSA or powdered milk, to saturate the binding sites thereon. Thereafter, the substrate is washed with a buffered solution and thereafter the buffer is removed. A specimen, e.g., human sera diluted with animal sera is added to the substrate. The resultant mass is then incubated and washed. Thereafter, radiolabeled, e.g., iodinated, e.g., $I^{125}$, antibodies to human IgG or IgM is added to the mass. The resultant mass is then washed and counted, e.g., in a gamma-counter. If the count is higher than a count performed on a normal sera control, the specimen contains antibodies to the pre-S region of HBV.

It is believed that the above procedure for detection of antibodies to the pre-S region of HBV can be applied as a diagnostic tool in detecting hepatitis B virus infection.

The pre-S protein moiety appears to be directly involved in attachment of HVB to liver cells of the host. Similar proteins are likely to be involved in the attachment of other viruses, the target of which is the liver. For this reason, synthetic peptides corresponding to the pre-S protein, as well as antibodies to them, could serve as the basis for diagnostic assays of and vaccines against other hepatitis viruses reacting with the same liver receptors as does hepatitis B virus.

In the above described procedures involving radioimmunoassay (RIA), an enzyme linked antibody can replace the radiolabeled antibody and ELISA techniques can be preformed. Furthermore, fluorescence techniques can be employed in place of RIA or ELISA.

The labelling ("marking") of one of the reaction components can be brought about by use of a "marker" or "marker substance" such as by incorporation of a radioactive atom or group, or by coupling this component to an enzyme, a dyestuff, e.g., chromophoric moiety or a fluorescent group.

The components concerned are preferably labelled by coupling to an enzyme, since the estimation of this is much simpler than for example, the estimation of radioactivity, for which special apparatus is necessary.

The enzymes used are preferably those which can be colorimetrically, spectrophotometrically, or fluorimetrically determined. Non-limiting examples of enzymes for use in the present invention include enzymes from the group of oxidoreductases, such as catalase, peroxidase, glucose oxidase, beta-glucuronidase, beta-D-glucosidase, beta-D-galactosidase, urease and galactose oxidase.

The coupling of the enzyme and the immunological component can be brought about in a known way, for example, by the formation of an amide linkage by methods known from peptide chemistry.

The labelling with a radioactive isotope can also be performed in a known way. Isotopes useful for labelling are predominantly $I^{125}$, $I^{131}$, $C^{14}$, and $H^3$.

The incubation steps utilized in carrying out the above procedures can be effected in a known manner, such as by incubating at temperatures of between about 20° C. and about 50° C. for between about 1 hour and about 48 hours.

Washings as described above are typically effected using an aqueous solution such as one buffered at a pH of 6-8, preferably at a pH of about 7, employing an isotonic saline solution.

The present invention also concerns diagnostic test kits for conducting the above-described methods for detecting antigens and antibodies.

A diagnostic test kit according to the present invention for detecting antigens coded for the pre-S gene of HBV in a test sample, would include the following:

a. a solid substrate coated with antibodies to a peptide having an amino acid chain corresponding to at least six consecutive amino acids within the pre-S gene coded region of the envelope of HBV, the peptide free of an amino acid sequence corresponding to the naturally occurring proteins of HBV, b. a protein-containing solution to saturate protein binding sites on the solid substrate, and c. a given amount of radiolabeled antibody, such antibody to either the peptide or HBsAg.

A diagnostic test kit according to the present invention for detecting antibodies to the pre-S region of hepatitis B virus in a test sample, would include the following:

a. a solid substrate having adsorbed thereon a peptide having an amino acid chain corresponding to at least six consecutive amino acids within the pre-S gene coded region of the envelope of HBV, the peptide free of an amino acid sequence corresponding to the naturally occurring proteins of HBV, the substrate being exposed to a protein-containing solution to saturate protein binding sites on the solid substrate, and b. a given amount of radiolabeled antibodies to human IgG or IgM.

Radiolabeled antibodies used in the above-described test kits can be packaged in either solution form, or in lyophilized forms suitable for reconstitution.

In the above test kits, enzyme or fluorescent labelled antibodies can be substituted for the described radiolabeled antibodies.

The above described process and test kit for detection of antibodies to the pre-S region of hepatitis B virus can be utilized in many applications, such as (1) detecting HBV infection in a patient by taking serum from the patient and applying the above described test or using the above described test kit; and (2) predicting recovery from HBV infection by taking serum from an infected patient and applying the above described antibody detection procedures.

The above described test procedure and test kit for antibody detection can be used for making qualitative comparisons between different HBV vaccines by taking serum from vaccinated patients and then utilize the above-described test procedure or kit for antibody detection. In general all known immunoassays using this antigen as reagent can be performed using the synthetic peptide of this invention. Generally all known immunoassays using antibody containing serum or reagents can be performed using antibody serum produced through the use of a synthetic peptide of this invention. These immunoassays included all those disclosed by Langone and Van Vunakis, *Methods of Enzymology*, Academic Press, Volumes 70, 73 and 74. Those assays disclosed in the disclosures of the following U.S. Pat. Nos. 4,459,359; 4,343,896; 4,331,761; 4,292,403; 4,228,240; 4,157,280; 4,152,411; 4,169,012; 4,016,043; 3,839,153; 3,654,090 and Re 31,006 and volumes 70, 73 and 74 of *Methods of Enzymology* are incorporated herein by reference.

A hepatitis B vaccine can be prepared by directly using a conjugate of a lipid vesicle and a peptide containing an amino acid chain corresponding to at least six consecutive amino acids within the pre-S gene coded region of the surface antigen of hepatitis B virus in an appropriate buffer. The conjugate having peptide in the appropriate concentration can be used as a vaccine with or without an adjuvant, such as, e.g., aluminum hydroxide or others.

The active component of the vaccine can be employed with a physiologically acceptable diluent (medium), e.g., phosphate buffered saline. Generally speaking, the synthetic peptide concentration in a physiologically acceptable medium will be between approximately less than 1 miligram and more than 10 micrograms per dose.

The vaccine can be prepared and used in the same general manner as disclosed in U.S. Pat. No. 4,118,479, the entire contents of which are incorporated by reference herein.

The vaccine can be administered by subcutaneous, intradermal or intramuscular injection. While the preferred route would depend upon the particular vaccine, it is believed that intramuscular injection will be generally suitable. Frequency of administration will vary depending upon the vaccine. Generally speaking, the vaccine will be administered in two doses about one month apart followed by a booster at six months to one year after primary immunization. The subsequent doses or the booster will depend on the level of antibody in the blood as a result of the initial immunization, and in certain instances may be unnecessary.

The hepatitis vaccine of the present invention is recommended for all persons at risk of developing hepatitis B infection and particularly those at especially high risk such as patients and staff on hemodialysis unit, medical personnel, persons of tropical populations and those visiting the tropics. In the case of tropical populations, particularly in Africa, Asia, the Mediterranean region and South America, where high incidence of hepatitis B infections has been consistently observed, the vaccine should be administered sufficiently early in life to prevent acquisition of chronic carrier state infection which tend to occur in these regions within the first five years of life. In fact, the vaccine is expected to be useful for all persons not already protected against hepatitis B infections as a result of prior immunity.

In order to more fully illustrate the nature of the invention and the manner of practicing the same, the following non-limiting examples are presented:

EXAMPLES

EXAMPLE 1

SDS-Polyacrylamide Gel Electrophoresis of HBsAg

About 20 and 200 μg, respectively, of HBsAg were separately electrophoresed for silver staining and transfer to nitrocellulose, respectively. Before electrophoresis, HBsAg was treated for 30 minutes at 37° C. with 2-mercaptoethanol and $NaDodSO_4$ (10 mg/ml each in 8M urea, 0.0625M Tris, pH 7.2). Similar results were obtained with HBsAg alkylated with iodoacetate after reduction. HBsAg was purified and radiolabeled as described (A. R. Neurath, N. Strick, C. Y. Huang, *Intervirology*, 10, 265 (1978)).

SDS-Polyacrylamide gel electrophoresis ("SDS-PAGE") was carried out following published procedures. See V. K. Laemmli, *Nature* (London), 227, 680 (1970). However, in order to maintain proteins in fully denaturated form, 8M urea was utilized in the running buffers in electrophoresis.

Polypeptides separated by SDS-PAGE were transferred to nitrocellulose using the TE 42 Transphor unit 9 (Hoefer Scientific Instruments, San Francisco, Calif.) following the procedure recommended by the manufacturer. The transferred proteins were tested for determinants reacting with antibodies to intact HBsAg (anti-HBs) using $^{125}I$-labeled human anti-HBs supplied as part of a commercial test kit (Abbott Laboratories, North Chicago, Ill.) as described (J. C. McMichael, L. M. Greisiger, L. Millman, *J. Immunol. Meth.*, 45, 79, (1981)).

From the 20 μg sample gel, separated HBsAg polypeptides (their $M_r$ given in kilodaltons) were stained by silver in situ (J. H. Morrissey, *Anal. Biochem*, 117, 307, (1981)), (see FIG. 1, Panel a) to yield two major and several minor polypeptides as expected. The separated polypeptides from the other 200 μg sample gel was then electrophoretically transferred to nitrocellulose, reacted (probed) with $^{125}$I-labeled antibodies to intact HBsAg (anti-HBs) and submitted to autoradiography (FIG. 1b).

Surprisingly, the 33 and 36 kilodalton (P33 and P36), rather than the two most abundant polypeptides reacted preferentially with anti-HBs (FIG. 1, Panel b). This suggested the presence of disulfide bond independent antigenic determinants reacting with anti-HBs on amino acid sequences which are not coded for by the S-gene of HBV DNA. P33 and P36 contain the sequence corresponding to the product of the S-gene and additional 55 residues at the amino-terminal part starting with Met at position 120 in the pre-S gene region (See FIG. 2).

EXAMPLE 2

Figure 3:
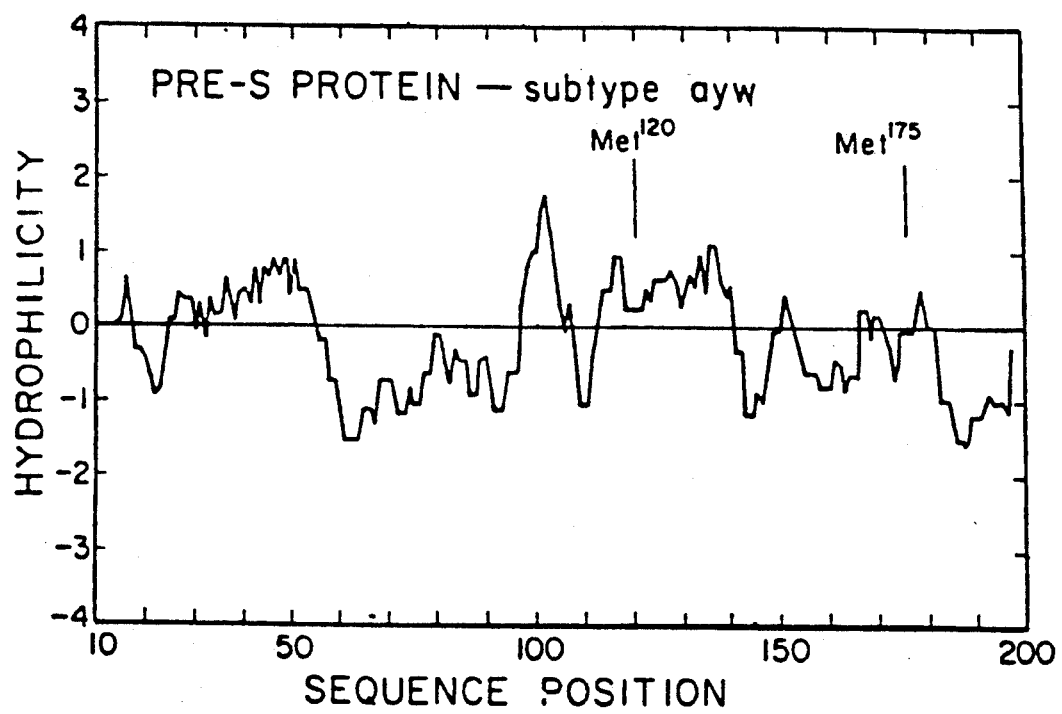
FIG. 3 shows a profile of relative hydrophilicity corresponding to the amino acid sequence of the pre-S gene product. Profiles for subtypes other than ayw are similar. The portion of the profile to the right from methionine 175 represents the S-gene translation product.

Synthesis Of A Peptide Mimicking Antigenic Determinants Corresponding To Residues 120-145 Of The Pre-S Gene Product The location of antigenic determinants on proteins may be predicted from computing the relative hydrophilicity along the amino acid sequence. See T. P. Hopp, K. R. Woods, *Proc. Natl. Acad. Sci. USA*, 78, 3824 (1981) and J. Kyte, R. F. Doolittle, *J. Mol. Biol.*, 157, 105 (1982). Results of such computation (J. Kyte et al supra) for the translation product of the pre-S region are shown in FIG. 3 and suggest the location of antigenic determinants in the sequence to the right from Met 120 within residues 120-140. The segment corresponding to residues 120-145 (FIG. 2) (pre-S 120-145, subtype adw$_2$) was selected for synthesis.

A C-terminal Cys(-SH containing) residue was added to allow unambiguous conjugation to carrier molecules and affinity matrices, while leaving the N-terminal unblocked as it may be in the intact protein. The molecule contains one Tyr and can therefore be radiolabeled. The Tyr could also be used for conjugation, although it might be a part of the antigenic determinant.

The peptide was synthesized by an accelerated version of stepwise solid phase peptide synthesis on the benzhydrylamine-type resin of Gaehde and Matsueda (*Int. J. Peptide Protein Res.*, 18, 451, (1981)) using Boc—NH—CH(phenyl)-phenyl—OCH$_2$COOH to derivatize NH$_2$CH$_2$-Resin (A. R. Mitchell, S. B. H. Kent, M. Engelhard and R. B. Merrifield, *J. Org. Chem.*, 43, 2845-2852, (1978)). After the Cys was coupled, the protected peptide chain was assembled according to the following protocol:

1. Deprotection: 65% v/v trifluoroacetic acid in dichloromethane, 1×10 minutes;
2. Wash: a flowing stream of dichloromethane was run over the resin under suction from an aspirator for 20 seconds;
3. Neutralization: 10% v/v diisopropylethylamine in dichloromethane, 2×1 minutes;
4. Wash: a flowing stream of dichloromethane was run over the resin under suction from as aspirator for 20 seconds;
5. Coupling: 2 mmol tert.Boc-L-amino acid in 2 ml dichloromethane was added to the neutralized resin followed immediately by 1 mmol dicyclohexylcarbodiimide in 2 ml dichloromethane; after 10 minutes a sample of resin (approximately 5 mg) was taken for determination of coupling yield by quantitative ninhydrin, and 10 ml dimethylformamide was added and the coupling continued. (Asn and Gln were coupled in the presence of hydroxybenzotriazole).
6. After the ninhydrin determination of a satisfactory coupling, the resin was washed as in step 4, above. For the addition of subsequent residues, the cycle was repeated. If recoupling was necessary, steps 3-5 were repeated. The synthesis was performed on a 0.5 mmol scale (0.5 gram aminomethyl-resin of 1 mmol/g loading). All volumes were 10 ml except where noted.

Protected amino acid derivatives used were N-alpha-tert.butyloxycarbonyl protected and side chain protected as follows: Arg(N$^G$Tosyl); Cys(4MeBzl); Tyr(BrZ); Asp(OBzl); Thr(Bzl); His(ImTosyl). Met and Trp were unprotected on the side chains. In another synthesis, otherwise identical, use of His(ImDNP) and Trp(InFormyl) gave purer product.

Assembly of the peptide chain was monitored by the quantitative ninhydrin reaction (V. K. Sarin, S. B. H. Kent, J. P. Tam, R. B. Merrifield, *Anal. Biochem*, 117, 147-157, (1981)) and was without difficulty except for the addition of the histidine residue which was 10% incomplete despite repeated couplings, presumably due to an impure amino acid derivative. After assembly of the protected peptide chain, the N-terminal Boc group was removed by trifluoroacetic acid treatment and the resin neutralized as in steps 1-4 above. Then the peptide was cleaved and deprotected by a 1 hour treatment at 0° C. with HF containing 5% v/v p-cresol and 5% v/v p-thiocresol to give the desired peptide as the C-terminal cysteinamide. Where His(ImDNP) was used, the DNP was removed by treatment with phenylphenol prior to HF cleavage. Where TrP (InFormyl) was used, HF conditions were adjusted to remove the Formyl group; either HF containing 10% anisole and 5% 1,4-butanedithiol, or HF containing p-cresol and 5% 1,4-butanedithiol. The product was precipitated and washed by the addition of ether, then dissolved in 5% v/v acetic acid in water and lyophilized to give a fluffy white solid.

Quantitative Edman degradation (H. D. Niall, G. W. Tregear, J. Jacobs, *Chemistry and Biology of Peptides*, J. Meienhofer, Ed (Ann Arbor Press, Ann Arbor, Mich., 1972), pp. 659-699) of the assembled peptide-resin revealed a high efficiency of chain assembly (S. B. H. Kent, M. Riemen, M. LeDoux, R. B. Merrifield, *Proceedings of the Fourth International Symposium on Methods in Protein Sequence Analysis*, M. Elzinga, Ed. (Humana, Clifton, N.J., 1982), pp. 626-628) which proceeded at a≧9./9.7 percent efficiency at each step, except for histidine at sequence position pre-S 128. HPLC of the peptide cleaved off the resin revealed a single major peak corresponding to approximately 85 percent of peptide material absorbing light at 225 nm.

EXAMPLES 3-6

Immunologic Properties Of A Peptide Mimicking Antigenic Determinants Corresponding To Residues 120-145 of the Pre-S Gene Product (pre-S 120-145)

EXAMPLE 3

Immunization

Figures 4A, 4B:
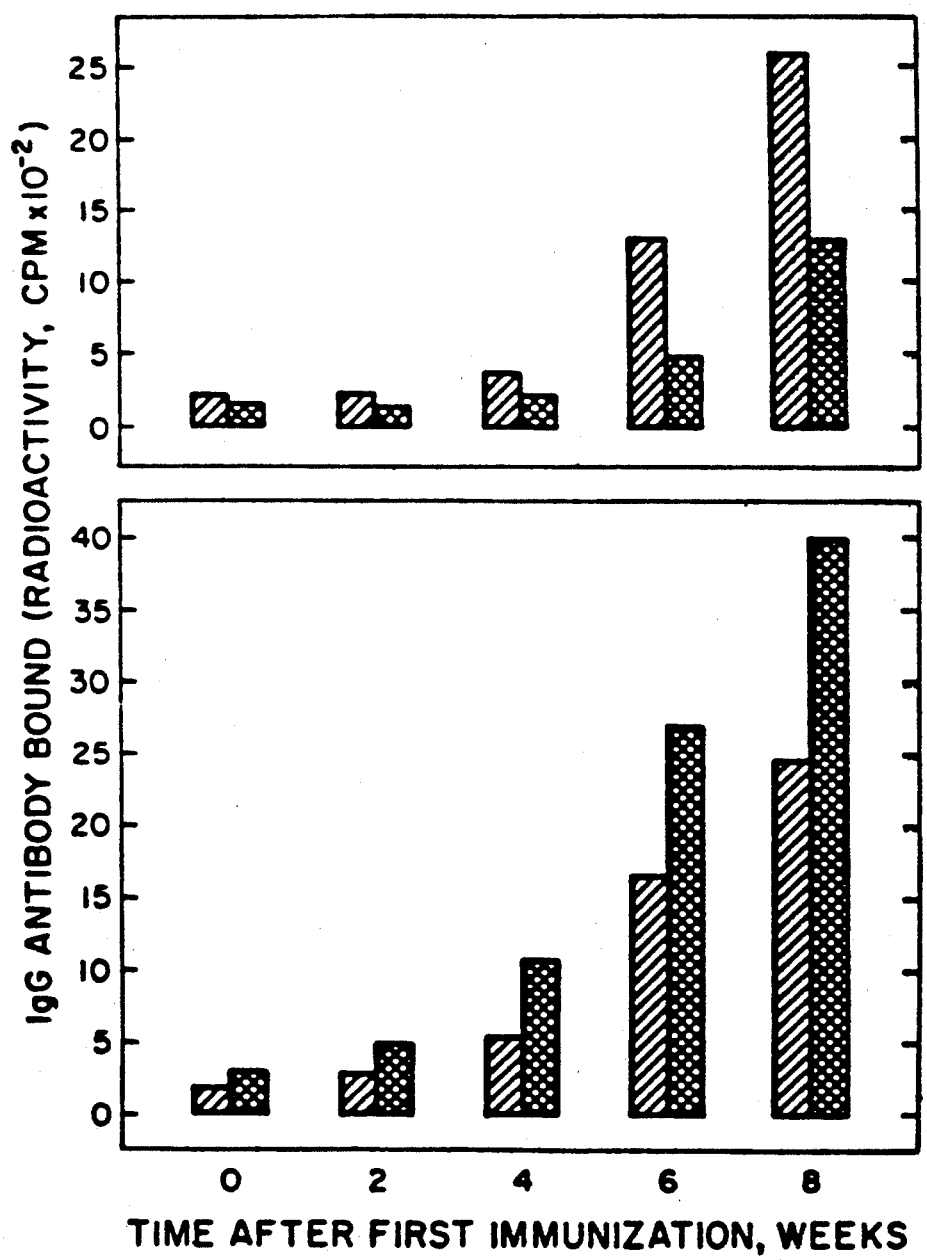
FIG. 4 shows two sets of bar graphs for mean antibody responses of rabbits immunized with free pre-S 120–145 (FIG. 4A) and with the same peptide linked to cross-linked liposomes containing L-tyrosine-azobenzene-p-arsonate (RAT) groups (FIG. 4B). Anti-HBs (antibodies to HBsAg), cross-hatched columns; anti-pre-S 120–145, diagonally hatched columns. Similar results to FIG. 4B were obtained with liposomes lacking RAT groups, except that responses after six weeks were lower. Columns corresponding to time=0 represent sera before immunization.

Immunization of rabbits with either free or carrier-bound pre-S 120-145 (subtype adw$_2$) were conducted and resulted in an antibody response in all animals against both the homologous peptide and HBsAg (FIG. 4).

The peptide corresponding to the amino acid sequence 120-145 (pre-S 120-145) of the pre-S region of HBV DNA (subtype adw$_2$; P. Valenzuela, P. Gray, M.

Quiroga, J. Zaldivar, H. M. Goodman, W. J. Rutter, *Nature* (London), 280, 815, (1979)) containing an additional Cys residue at the C-terminal, added for convenience of coupling to carriers, was synthesized by an improved solid phase technique (S. B. H. Kent, *Biomedical Polymers*, E. P. Goldberg, A. Nakajima, Eds. (Academic, N.Y., 1980), pp. 213–242; A. R. Mitchell, S. B. H. Kent, M. Engelhard, R. B. Merrifield, *J. Org. Chem.* 43, 2845, (1978); and S. Mojsov, A. R. Mitchell, R. B. Merrifield, *J. Org. Chem.*, 45, 555 (1980).

For immunoassays and linking to carriers the peptide was treated with 2-mercaptoethanol and separated from low $M_r$ components by chromatography on Sephadex G-10 (A. R. Neurath, S. B. H. Kent, N. Strick, *Proc. Natl. Acad. Sci. USA*, 79, 7871 (1982)).

Groups of two to three rabbits were immunized with either free pre-S 120–145 or with the peptide linked to cysteine-activated liposomes containing stearylamine, dilauroyl lecithin and cholesterol which had been fixed with glutaraldehyde, and either did or did not have attached RAT groups for enhancing antibody responses to haptens (A. R. Neurath, S. B. H. Kent, N. Strick, *J. Gen. Virol.*, in press (1984)). The immunization schedule involving the use of complete and incomplete Freund's adjuvant was the same as described (Neurath, Kent, Strick, et al (1984) supra). Antibodies to HBsAg in sera of rabbits immunized with pre-S 120–145 were tested by a double-antibody radioimmunoassay (RIA) using HBsAg-coated polystyrene beads and $^{125}$I-labeled anti-rabbit IgG (Neurath, Kent, Strick, et al (1984) supra).

Antibodies to the homologous peptide were tested by a similar test except that 2.5 mg of a cellulose-peptide conjugate were used instead of coated beads. This conjugate was prepared in the following way: 0.5 g of sulfhydryl cellulose, prepared as described (P. L. Feist, K. J. Danna, *Biochemistry*, 20, 4243 (1981)), were suspended in 5 ml 0.1M sodium acetate, pH 5, and mixed with 2.5 ml of 0.25M N-N'-p-phenylenedimaleimide in dimethylformamide for one hour at 30° C. and then washed with 0.1M phosphate-10 mM EDTA, pH 7.0. The cellulose derivative was suspended in 10 ml of the latter buffer containing 5 mg of pre-S 120–145 and mixed for at least sixteen hours at 20° C. The cellulose derivative was extensively washed and suspended in 0.14M NaCl-10 mM Tris-3 mM NaN$_3$ (TS). The final preparation contained 8 mg of pre-S 120–145 per g of cellulose.

EXAMPLE 4

Figure 5:
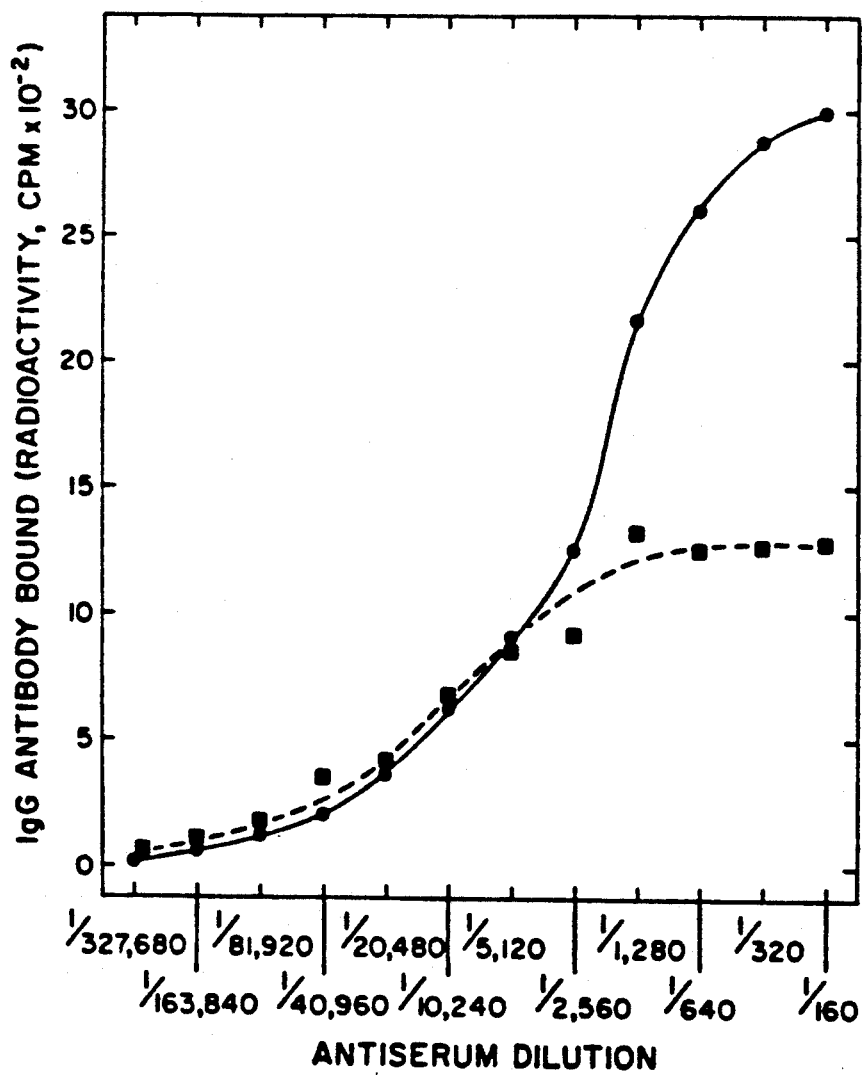
FIG. 5 depicts radioimmunoassays with serial dilutions of a serum from a rabbit immunized with pre-S 120–145 linked to liposomes. Anti-HBs (antibodies to HBsAg), ■; anti-pre-S 120–145, ●. Counts per minute (cpm) corresponding to distinct dilutions of the pre-immune serum were subtracted from cpm corresponding to dilutions of anti-pre-S 120–145; the difference was plotted. The endpoint titer of the serum (1/163,840) corresponds to its highest dilution at which the cpm were ≧2.1 higher than those corresponding to the same dilution of the pre-immune serum.

Radioimmunioassays were conducted with several dilutions of a serum from one of the rabbits immunized with pre-S 120–145 linked to liposomes (See FIG. 5).

Antibodies were still detectable when the antisera were diluted up to $1.6 \times 10^5$-fold (FIG. 5).

Pre-S 120–145 or anti-pre-S 120–145 inhibited the reaction between $^{125}$I-labeled anti-HBs and P33 (P36). $^{125}$I-labeled HBsAg was immunoprecipitated with anti-pre-S 120–145 at all dilutions positive by RIA (FIG. 5). HBV particles reacted with anti-pre-S 120–145 as determined by detection of HBV-DNA within the immune complexes and by electron microscopy (A. R. Neurath, N. Strick, L. Baker, S. Krugman, *Proc. Nat. Acad. Sci. USA*, 79, 4415 (1982)).

EXAMPLE 5

Anti-Peptide Antibody as A Specific Probe for Detection of P33 and P36

Figure 6:
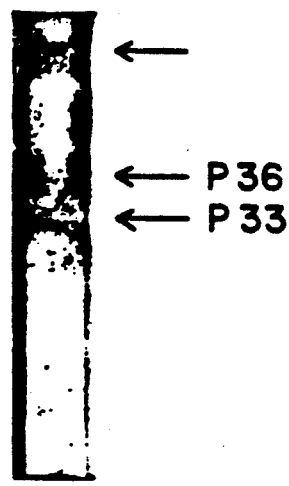
FIG. 6 is a pen & ink drawing that shows the reaction of anti-pre-S 120–145 with P33 and P36 in a Western blot (similar to FIG. 1).

Anti-pre-S 120–145 was reacted with P33 and P36. HBsAg polypeptides separated by SDS-PAGE run in urea were transferred to nitrocellulose, reacted with anti-pre-S 120–145 diluted 1/80 in TS containing 10 mg/ml of bovine serum albumin and 2.5 mg/ml of gelatine (TS-BG) for five hours at 20° C. To detect bound IgG, the nitrocellulose sheet was washed and exposed to $^{125}$I-labeled protein A (0.4 μC/100 ml TS-BG) for five hours at 20° C. For further details see FIG. 1. In FIG. 6, arrows indicate the positions of P33 and P36. The top arrow (corresponding to a molecular weight of 66 kilodaltons) indicates another protein reacting with anti-pre-S 120–145, possibly corresponding to a dimer of P33.

EXAMPLE 6

Figure 7:
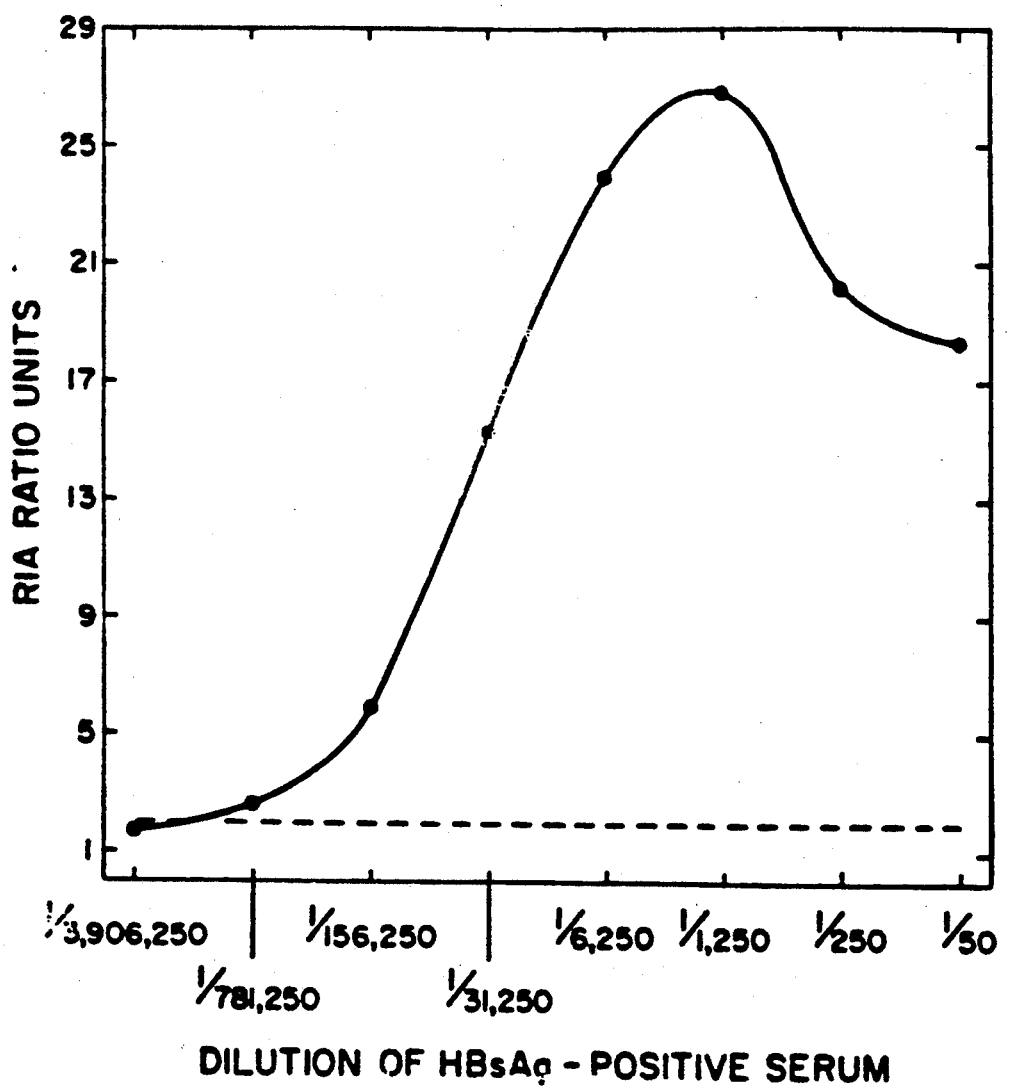
FIG. 7 shows a graph depicting a diagnostic test for hepatitis B antigens based on polystyrene beads coated with anti-pre-S 120-145.

Development Of A Diagnostic Test For The Detection Of Antigens Coded For By The Pre-S Gene In Sera Of HBV-Infected Individuals FIG. 7 shows the results of a diagnostic test based on polystyrene beads coated with anti-pre-S 120–145.

Serial dilutions of an HBsAg-positive serum in a mixture of normal human and rabbit serum each diluted 1/10 in TS were tested. $^{125}$I-labeled human anti-HBs (Abbott Laboratories) was used in the test performed essentially as described for the AUSRIA II diagnostic kit (Abbott Laboratories). Results are expressed as RIA ratio units, determined by dividing cpm corresponding to positive samples by cpm corresponding to positive samples by cpm corresponding to normal serum controls. The endpoint titer corresponds to the highest dilution at which the RIA ratio was 2.1 (broken line). The endpoint titer of the serum as determined by the AUSRIA test was approximately $1/10^6$. Negative results were obtained with control beads coated with normal rabbit IgG.

Similar results were obtained with sera containing HBsAg subtypes ad and ay, indicating that the synthetic peptide with the sequence corresponding to subtype adw (FIG. 2) carried common group-specific antigenic determinants.

EXAMPLE 7

Synthesizing and Testing S(135–155) Derivatives

Each of the conjugates ((1) to (26)) of S(135–155) listed in Table 1, except conjugate 3, was mixed 1:1 with complete Freund's adjuvant and injected into two New Zealand White rabbits (65 to 160 μg of peptide per rabbit). The rabbits were further injected at biweekly intervals with equal doses of conjugates in incomplete Freund's adjuvant (not used for conjugate 3). Blood specimens were taken two weeks after each injection.

To prepare conjugates 1, and 4–8 (Table 1), 1 mg quantities of peptide 309–329 of the env gene product (S(135–155)) were activated with a two times molar excess of N-ethyl-N' (dimethyl-aminopropyl) carbodiimide (EDAC) and N-hydroxy-benzotriazole (NHBTA) and subsequently linked to equimolar quantities of poly-D-lysine and diaminoalkanes (from Fluka AG, Buchs, Switzerland), respectively, as described (Arnon, R., Sela, M., Parant, M. and Chedid., L., "Antiviral Response Elicited By A Completely Synthetic Antigen With Built-In Adjuvanticity", *Proceedings of The National Academy of Science USA*, 77, 6769-6772, (1980)). To prepare conjugates 2 and 3, 1 mg quantities of each EDAC-activated S(135-155) and MDP (Calbiochem, San Diego, Calif.) were linked to 10 mg of poly-D-lysine. Peptide 309-329 of the env gene product (800 μg) was oxidized with ferricyanide (Dreesman et al, 1982 supra), activated with EDAC as above and linked to 4 mg of LPH. Chromatography on Sephadex G-25 indicated complete linking of the peptide to LPH (conjugate 9). The oxidized, EDAC-activated peptide (1 mg) was also conjugated to 1 mg of polyvaline in a suspension of 2.5 ml of 1M NaHCO$_3$, pH 8.5, and 10 ml of CHCl$_3$. The interphase and aqueous phase after centrifugation was used for immunization (conjugate 10).

Liposomes were prepared by the method of Oku, N. Scheerer, J. F., and MacDonald, R. C., "Preparation of Giant Liposomes", *Biochimica et Biophysica Acta*, 692, 384-388 (1982). Stearylamine, dilauroyl lecithin and cholesterol were dissolved in glucose-saturated ethanol at final concentrations of 10, 23 and 1.43 mg/ml, respectively. For some liposome preparations, the concentration of dilauroyllecithin was decreased to 17.5 mg/ml and sphingomyelin was added (10 mg/ml). Other preparations contained as an additional component lipid A (420 μg/ml; Calbiochem). The solutions were dialyzed against 0.1M NaCHO$_3$, pH 8.5, in dialysis bags with a molecular weight cut-off of 10$^3$ daltons for at least sixteen hours. The liposomes were treated for approximately six hours with glutaraldehyde (final concentration 30 mg/ml), mixed with 0.5 volumes of 33.9% (w/w) sodium diatrizoate, floated four times into 1M NaCHO$_3$ by centrifugation for ten minutes at 10,000 rpm, and reacted with 0.84 to 1 mg of peptide 309-329 of the env gene product per 10 mg stearylamine overnight at 20° C. The linking of peptide 309-329 of the env gene product to liposomes under these conditions was complete. Some preparations were reacted additionally with 7.5 mg of RAT (Biosearch, San Rafael, Calif.) per 10 mg of stearylamine for six hours at 20° C. The liposomes were floated three times into 0.14M NaCl, 0.01 Tris-HCl-0.02% NaN$_3$ (TS) and dialyzed against TS-10$^{-4}$M oxidized glutathione for at least sixteen hours.

In some cases (20) and (21) the stearylamine-containing liposomes were not derivatized with GA but instead directly reacted with EDAC-activated peptide 309-329 of env gene product. Alternately, (18) and (19), the activated peptide 309-329 of env gene product was linked to glutaraldehyde-treated liposomes further derivatized by reaction with 0.2M ethylene diamine at pH 8.5 overnight at 20° C. followed by floating two times into 0.1M NaHCO$_3$, pH 8.5, reduction with 10 μM sodium dithionite for one hour at 20° C. and repeated floating into the same buffer. An aliquot of these liposomes was additionally reacted with EDAC-activated RAT. The liposomes were finally dialyzed against TS-10$^{-4}$M oxidized glutathione.

In one preparation (22), stearic acid was used instead of stearylamine for the preparation of liposomes. These were dialyzed against 0.01M NaCl, activated with EDAC (50 mg/ml for two hours plus additional 25 mg/ml for one hour) at pH 5.5 and 20° C., floated two times into 0.01M NaCl and reacted with the peptide 308-329 of the env gene product in 1M NaHCO$_3$, pH 8.5, overnight.

Polyglutaraldehyde microspheres were prepared as described by Margel, S., Zisblatt, S. and Rembaum, A. "Polyglutaraldehyde: A New Reagent For Coupling Proteins To Microspheres And For Labeling Cell-Surface Receptors. II. Simplified Labeling Method By Means Of Non-Magnetic And Magnetic Polyglutaraldehyde Microspheres", *Journal of Immunological Methods*, 28, 341-353 (1979), using Polysurf 10-36 B (Bartig Industries Inc., New Canaan, Conn., Margel & Offarim, (1983)). One mg of the peptide 309-329 of the env gene product was linked to approximately 50 mg of microspheres under conditions similar to those described for glutaralde-hyde treated liposomes. Conjugate 25 was prepared by treating the microspheres with 5 ml of 0.1Mε-amino caproic acid at pH 8.5 overnight. After centrifugation, the microspheres were suspended in dimethylformamide (2 ml) and reacted with 2 mg EDAC plus 670 ug NHBTA for one hour at 20° C. After centrifugation, the microspheres were resuspended in 2 ml of 0.1M NaHCO$_3$, pH 8.5, containing 1 mg of peptide 309-329 of the env gene product.

All reagents listed above were of analytical grade and obtained from Sigma, St. Louis, Mo., unless indicated otherwise.

Figure 8:
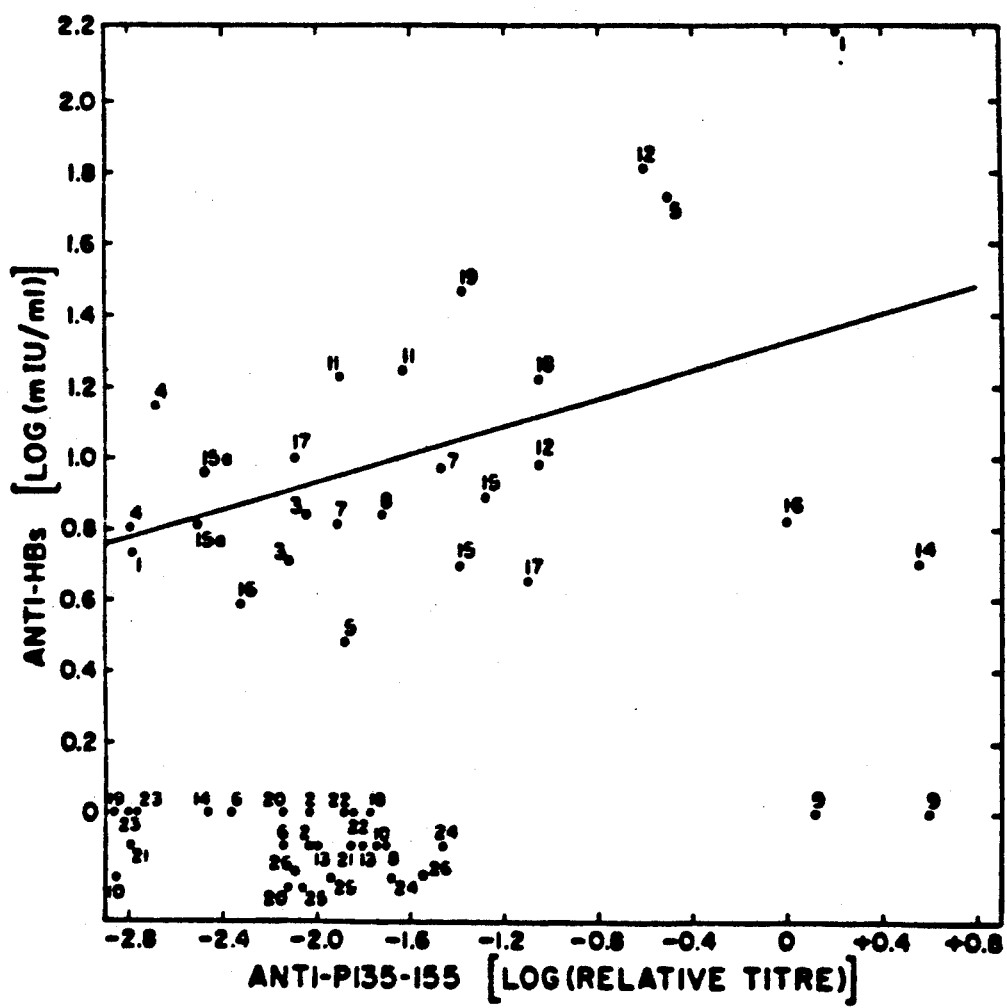
FIG. 8 depicts a plot representing the compilation of antibody responses of individual rabbits to conjugates of S135-155 (amino acids 309 to 329 of the open reading frame of the HBV env gene). The type of conjugates is indicated by numbers defined in Table 1. Antibodies in sera obtained two weeks after the third immunization were assayed using a S135-155-beta-galactosidase conjugate and Pansorbin (Neurath et al., 1982, supra). Their relative titer is given in comparison with antibody levels induced by a S135-155-KLH conjugate. Results of anti-HBs assays by RIA (AUSRIA test, Abbott Laboratories, North Chicago, Ill.) are given in international milli-units (mIU/ml; Neurath et al., 1982 supra). The line corresponds to the calculated linear regression that best fits the set of all data concerning rabbits with an anti-HBs response. The calculated correlation coefficient (=0.55) indicates a poor correlation between anti-HBs and anti-S135-155 responses.

Free peptide 309-329 of the env gene product (mol. weight=2,664 daltons) containing five cysteine residues was in a predominantly monomeric form since it was eluted after molecular exclusion chromatography in about the same fractions as insulin A chain. Linking to diaminobutane and to other diamino-alkanes (data not shown) resulted in formation of S(135-155) polymers which were immunogenic and induced both antipeptide and anti-HBs antibodies. Preparations (4), (5) and (7) also induced anti-HBs, while polymers with diaminooctane or dodecane linkers (6) and (8) failed to do so (FIG. 8) for reasons not known. Oxidation of the peptide 309-329 of the env gene product resulted in polymerization (data not shown). The polymer linked to LPH (conjugate 9) induced high levels of anti-S(135-155) but no anti-HBs, unlike S(135-155) linked to KLH or LPH in its reduced form (Neurath et al., 1982, supra). This finding again emphasizes the role of peptide conformation in inducing antibodies to the native protein. Linking of the oxidized peptide to highly hydrophobic poly-L-valine resulted in a conjugate (10) of low immunogenicity. S(135-155) linked to poly-D-lysine administered with Freund's adjuvant (1) or having covalently linked MDP and given without adjuvant (3) induced both anti-S(135-155) and anti-HBs. The latter conjugate administered with Freund's adjuvant (2) appeared poorly immunogenic. S(135-155) linked to glutaraldehyde treated liposomes containing stearylamine (conjugate 11) induced levels of anti-HBs comparable to those elicited by those elicited by conjugates with KLH or LPH (Neurath et al., 1982, supra). Incorporation of sphingomyelin and or lipid A, components reported to enhance the antigenicity of haptens inserted into liposomal membranes (Yasuda, T., Dancey, G. F. and Kinsky, S. C., "Immunogenicity Of Liposomal Model Membranes In Mice: Dependence On Phospholipid Composition", *Proceedings Of The National Academy Of Sciences*, 74, 1234-1236 (1977)), into the liposomes (conjugates 13, 15a, 16) failed to enhance anti-HBs, responses.

Conjugates (18 and 19) prepared by linking S(135-155) to glutaraldehyde-treated liposomes through an ethylenediamine bridge rather than directly, had the capacity to induce anti-HBs but a considerable variability in response between individual rabbits was observed.

S(135-155) before or after oxidation and subsequently linked to stearyl-amine-containing liposomes (not fixed with glutaraldehyde; preparations 20 and 21) or to stearic acid-containing liposomes (22) induced low levels of anti-S-135-155 and no measurable anti-HBs.

S(135-155) linked directly to microspheres of polyglutaraldehyde (preparations 23 and 24) induced a primary anti-HBs response. However, the level of anti-HBs decreased in the course of immunization. Anti-HBs was undetectable in sera collected two weeks after the third immunization. S(135-155) linked to these microspheres through ε-amino-caproic acid (25) and 1-cysteine (26) bridges, respectively, either failed (25) or was marginally efficient (26) in eliciting anti-HBs.

Figures 9A, 9B, 9C, 9D:
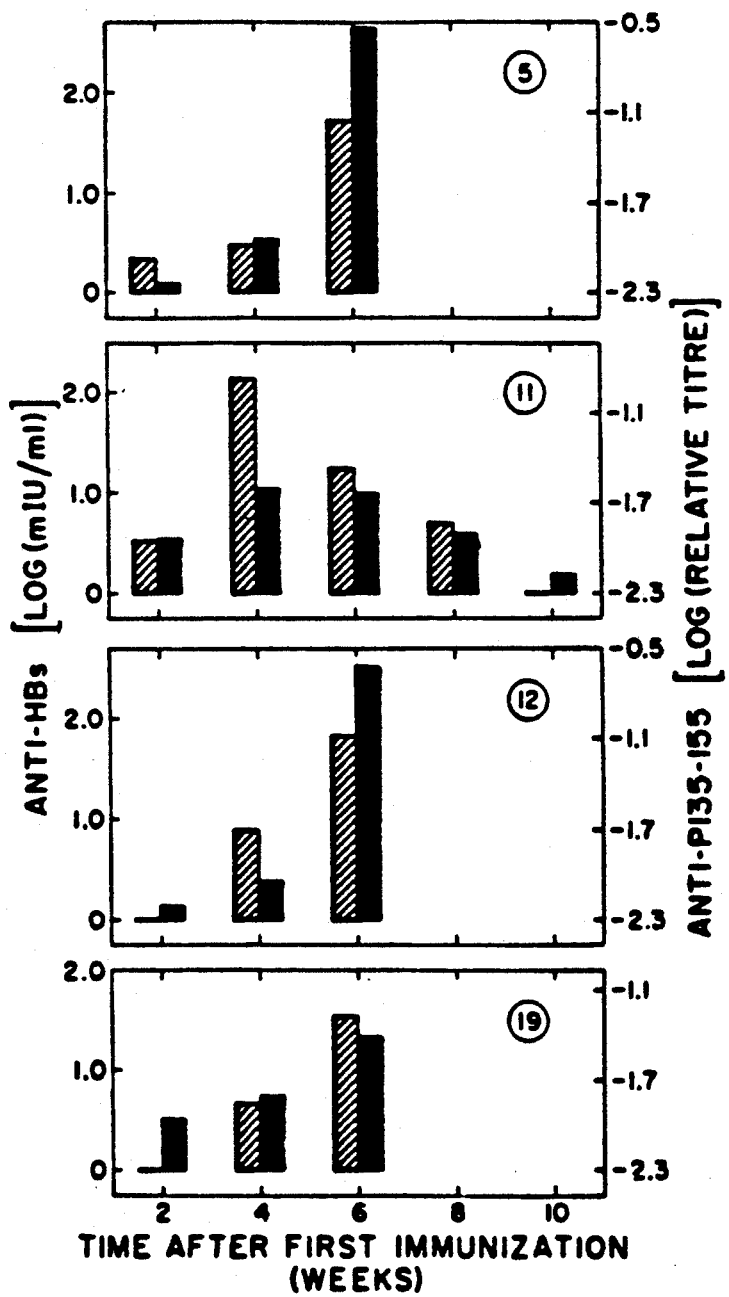
FIG. 9C and FIG. 9D) depicting examples of time courses of antibody responses in rabbits immunized with distinct S135-155-conjugates (indicated by numbers in each panel and defined in Table 1).
FIG. 9A corresponds to conjugate No. 5.
FIG. 9B corresponds to conjugage No. 11.

S(135-155)-KLH or LPH conjugates elicited a primary anti-HBs response but the level of anti-HBs failed to increase in sera of rabbits after additional antigen doses (Neurath et al., 1982 supra). With the conjugates described above, generally, a decrease of anti-HBs levels was observed four or six weeks after primary immunization (FIG. 9B), but exceptions were observed in a minority of rabbits (panel 5, FIG. 9A). This declining trend was uniformly reversed when RAT was inserted into liposomal membranes together with S(135-155) (for example FIG. 9C and FIG. 9D).

The immunogenicity of haptens inserted into liposomal membranes depends on the phospholipid composition of the liposomes and seemed to be inversely related to the fluidity of these membranes (Yasuda et al., 1977 supra; Dancey, G. F., Yasuda, T. and Kinsky, S. C., "Effect Of Liposomal Model Membrane Composition On Immunogenicity", *The Journal Of Immunology*, 120, 1109-1113 (1978)).

Treatment of stearylamine-containing liposomes with glutaraldehyde was found to provide reactive groups suitable for linking of synthetic peptides and at the same time increases the rigidity of the lipid membranes. Such liposomes, especially when containing carrier function enhancing RAT sites (Alkan, S. S., Nitecki, D. E. and Goodman, J. W., "Antigen Recognition And the Immune Response: The Capacity of 1-Tryosine-Azobenzenearsonate To Serve As A Carrier For A Macromolecular Hapten", *The Journal Of Immunology*, 107, 353-358, (1971), and Alkan, S. S., Williams, E. B., Nitecki D. E. and Goodman, J. W., "Antigen Recognition And the Immune Response. Humoral And Cellular Immune Responses To Small Mono- And Bifunctional Antigen Molecules", *The Journal Of Experimental Medicine*, 135, 1228-1246, (1972)), are a promising tool for preparing fully synthetic immunogens for eliciting antiviral antibodies.

TABLE 1

List of cross-linkers and carriers used for the preparation of S(135-155) conjugates

| | |
|---|---|
| (1) | Poly-D-lysine (mol. weight 3-7 × 10⁴) |
| (2) | 1 + N-Acetylmuramyl-L-alanyl-D-isoglutamine (MDP) |
| (3) | = 2 |
| (4) | 1,4-diaminobutane |
| (5) | 1,6-diaminohexane |
| (6) | 1,8-diaminooctane |
| (7) | 1,10-diaminodecane |
| (8) | 1,12-diaminododecane |
| (9) | Oxidized S(135-155) linked to LPH |
| (10) | Oxidized S(135-155) linked to poly-L-valine |
| (11) | Liposomes containing stearylamine, and treated with glutaraldehyde |
| (12) | = 11 = L-tyrosine-azobenzene-p-arsonate (RAT) |
| (13) | = 11 + Sphingomyelin (from bovine brain) |
| (14) | = 13 + RAT |
| (15a) | = 11 + Lipid A |

TABLE 1-continued

List of cross-linkers and carriers used for the preparation of S(135-155) conjugates

| | |
|---|---|
| (15) | = 15a + RAT |
| (16) | = 13 + Lipid A |
| (17) | = 16 + RAT |
| (18) | = 11 treated with ethylenediamine |
| (19) | = 18 + RAT |
| (20) | = Liposomes containing stearylamine reacted with oxidized S(135-155) (see 9) |
| (21) | = 20 except S(135-155) was oxidized after attachment to liposomes |
| (22) | Stearic acid containing liposomes |
| (23) | Polyglutaraldehyde microspheres |
| (24) | = 23 + RAT |
| (25) | = 23 treated with ε-aminocaproic acid |
| (26) | = 23 treated with L-cysteine |

EXAMPLE 8

A peptide pre-S (12-32) (subtype adw$_2$) was synthesized according to the procedure described hereinabove in Example 2. The free peptide, the peptide linked to glutaraldehyde cross-linked liposomes (±RAT groups) (according to the procedure described above in Example 7) as well as the peptide linked to KLH were used to immunize rabbits. The corresponding antibodies recognized not only the peptide, but also HBsAg and HBV. In view of the above, this peptide is believed quite useful for a vaccine against hepatitis B virus, and as the basis of useful HBV diagnostics based on either the peptide itself (to detect anti-HBV response in infected or immunized individuals), or on peptide antibodies to detect hepatitis B antigens.

EXAMPLE 9

A peptide pre-S (117-134) (subtype adw$_2$) was synthesized according to the procedure described hereinabove in Example 2.

EXAMPLE 10

A rabbit was immunized with the peptide pre-S (117-134) prepared according to Example 9 and linked to a carrier according to the procedure of Example 7. Such immunization was conducted according to the procedure described hereinabove in Example 3 and was found to produce antibodies in the serum of the rabbit so innoculated. However, the antibody titers were substantially less than those observed for the use of pre-S (120-145) and pre-S (12-32).

EXAMPLE 11

The immune response in rabbits to each of two synthetic peptides corresponding to residues 120-145 and 12-32 of the translational product of the pre-S gene of HBV DNA (subtype adw$_2$) was tested. Peptide pre-S (120-145) was prepared according to Example 2 and peptide pre-S (12-32) was prepared according to Example 8. Their sequences are: MQWNSTAFHQTLQDPRVRGLYLPAGG (pre-S (120-145)) and MGTNLSVPNPLGFFPDHQLDP (pre-S (12-32)). For immunization, the peptides were used in free form, employing alum or Freund's adjuvant, or linked to carriers, i.e., keyhole lympet hemocyanin (KLH) and cross-linked liposomes, respectively. The liposomes were prepared as described in Example 7.

Figure 10:
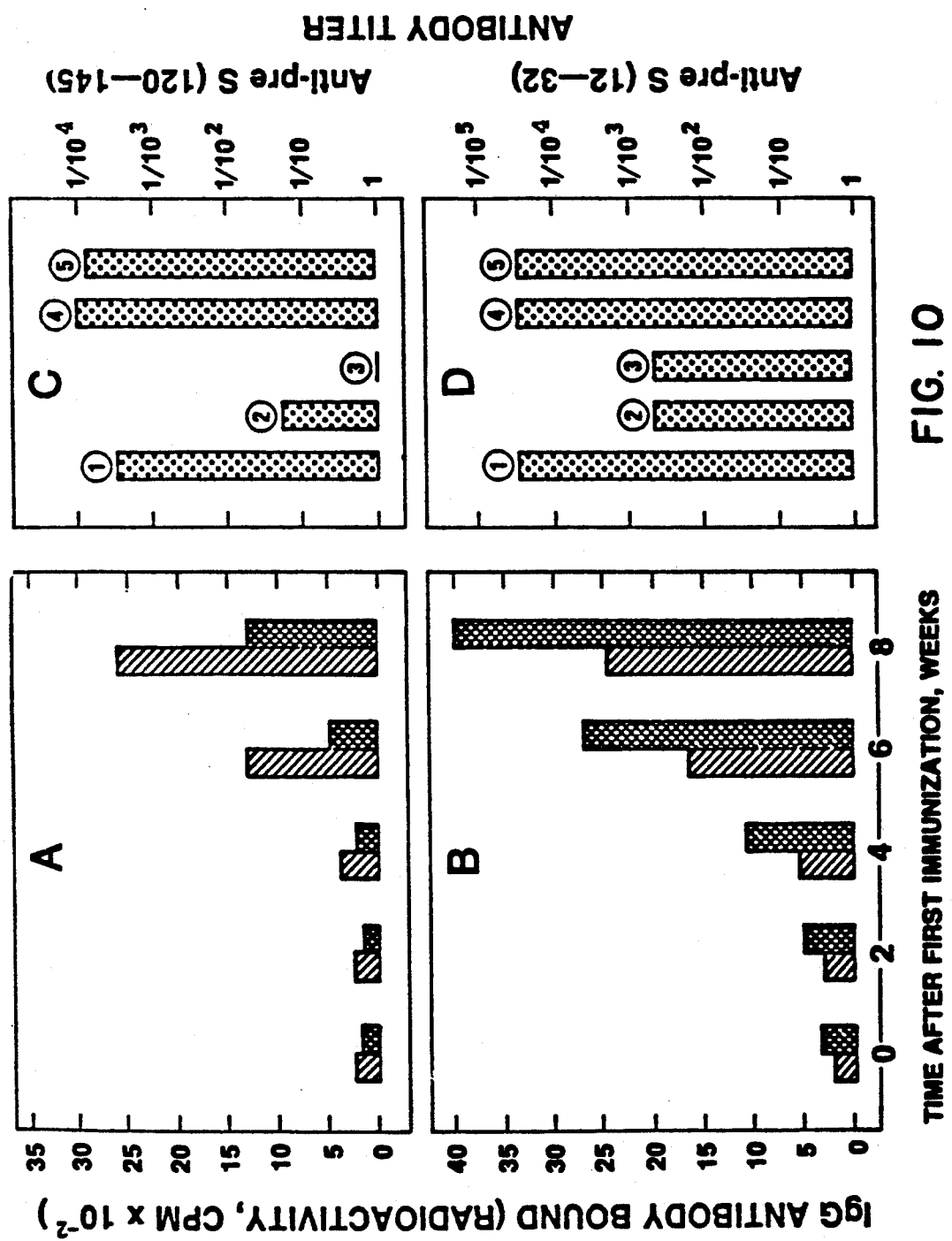
FIG. 10 shows four plots (A, B, C and D) which depict the kinetics of antibody responses to peptide pre-S(120-145) (□) and to pre-S protein within approximately 22 nm spherical HBsAG particles (■) elicited by unconjugated peptide pre-S(120-145) (plot A) and by the same peptide linked to cross-linked, cysteine-activated liposomes with attached RAT (L-tyrosine azobenzene-p-arsenate) groups (plot B); and the effect of carrier on anti-peptide antibody titers in sera of rabbits immunized with 4 doses of peptides pre-S(120-145) (plot C) and pre-S(12-32) (plot D) given 2 weeks apart. The carriers for plots C and D were:  1.  none;  2.  keyhold lympet hemocyanin (KLH);  3.  alum;  4.  and  5.  cross-linked, cysteine-activated liposomes with or without attached RAT groups. Complete and incomplete Freund's adjuvant was used in all cases except  3. .

The best results were obtained with peptides covalently linked to the surface of liposomes (see FIG. 10).

Immunization with KLH conjugates resulted in a high anti-KLH response (endpoint titers of 1/5,000,000 by radioimmunoassay), apparently causing low booster responses to the peptides. On the other hand, much lower antibody responses (approximately $1/10^3$) to RAT groups were detected, when RAT-containing liposomes were used as carriers. Antibodies to liposomes (lacking RAT) were undetectable. This suggests that liposomes are the carrier of choice for immunization with synthetic peptides.

EXAMPLE 12

To establish whether or not antigenic determinants corresponding to pre-S gene coded sequences are preferentially present on HBV particles, the reaction of antisera raised against HBV particles with the two synthetic peptides analogues of the pre-S protein was tested. The maxium dilutions of this antiserum at which antibodies reacting with the synthetic peptides were still detectable were: approximately 1/62,500 ($\frac{1}{2} \times 10^6$ with tests utilizing $^{125}$I-labeled protein A instead of labeled second antibodies), and approximately 1/2,560 for peptides pre-S(120-145) and pre-S(12-32), respectively (see FIG. 11). The antiserum (adsorbed on HBsAg-Sepharose to remove antibodies to S-protein) did not react with synthetic peptide analogues of the S-protein, peptide (309-329) of the env gene product (S(135-155)), peptide (222-239) of the env gene product (S(48-65)) and peptide (243-253) of the env gene product (S(69-79)) and was, therefore, specific for pre-S gene coded sequences. In comparison, the dilution endpoints of antisera prepared against the homologous peptides were approximately 1/300,000 and approximately 1/80,000 for anti-pre-S(120-145) (see FIG. 11) and anti-pre-S(12-32) (data not shown), respectively.

Figure 11:
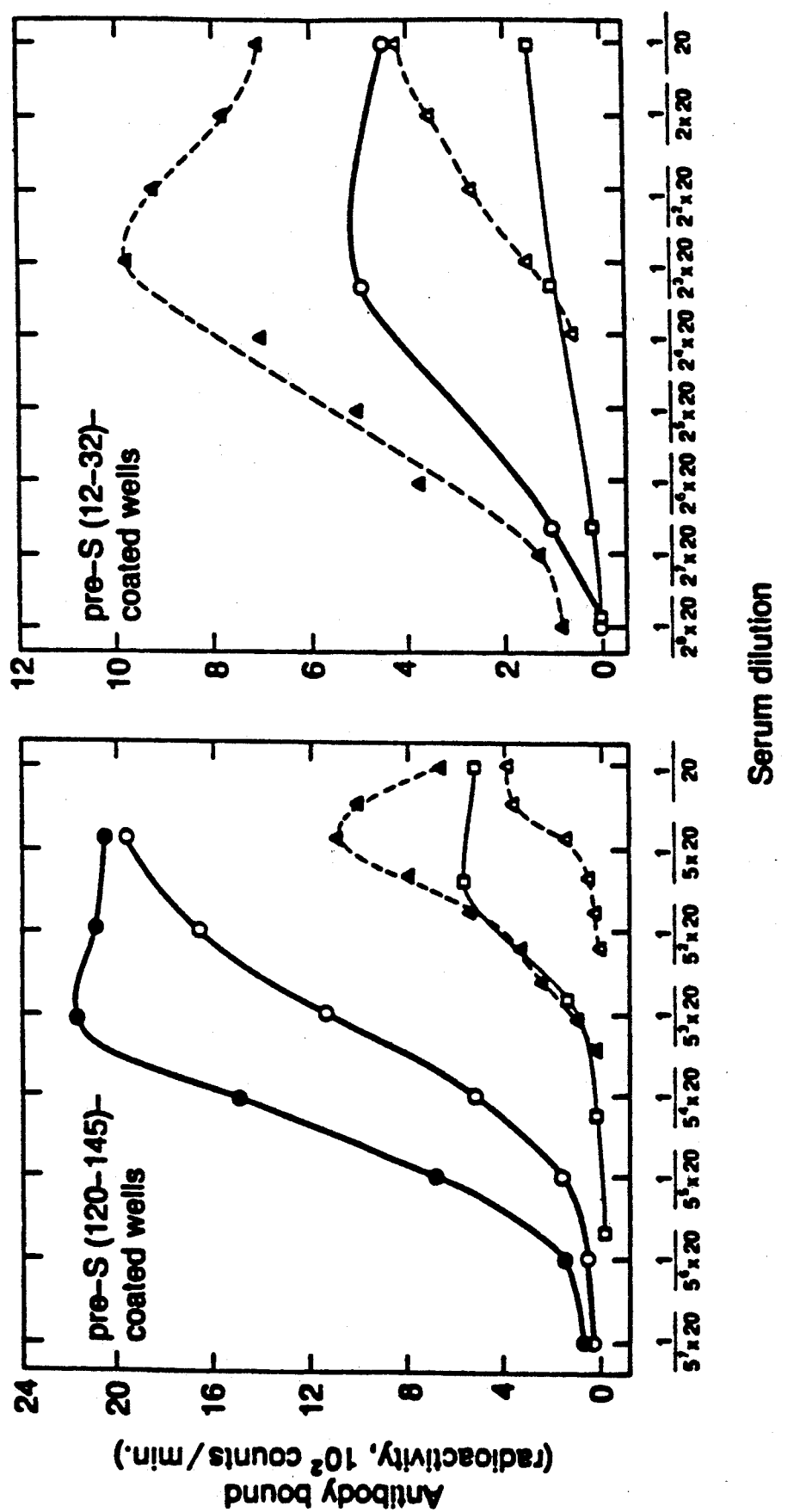
FIG. 11 shows two plots for radioimmunoassays of IgG antibodies in serial dilutions of rabbit antisera: to pre-S(120-145) [○]; to HBV particles and tubular forms of HBsAg [◯], devoid of antibodies to S-protein detectable by RIA and to a fusion protein of chloramphenicol acetyltransferase with the sequences of pre-S protein lacking the 41 C-terminal amino acid residues (□); and of IgG (△) and IgM (▲) antibodies in serum of a patient recovered from hepatitis B. The latter serum was drawn before antibodies to the S-protein were detectable. Immulon 2 Removable strips (Dynatech Laboratories) were coated with 20 μg/ml of either free peptide pre-S(120-145) or pre-S(12-32) and post-coated with gelatin (2.5 mg/ml in 0.1 M Tris, pH 8.8). The conditions for coating and the double antibody RIA are described in A. R. Neurath, S. B. H. Kent, N. Strick, *Science,* 224, 392 (1984) and A. R. Neurath, S. B. H. Kent, N. Strick, *Proc. Natl. Acad. Sci USA,* 79, 7871 (1982).

The synthetic peptides were recognized also by antibodies (IgG and IgM) in sera of individuals who had just recovered from acute hepatitis B, and by rabbit antibodies against a fusion protein between chloramphenicol acetyltransferase and a portion of pre-S protein expressed in *E. coli* (see FIG. 11).

On the other hand, humans vaccinated with pepsin-treaded HBsAg (M. R. Hilleman, E. B. Buynak, W. J. McAleer, A. A. McLean, P. J. Provost, A. A. Tytell, in *Viral Hepatitis,* 1981 *International Symposium,* W. Szmuness, H. J. Alter, J. E. Maynard, Eds. (Franklin Institute Press, Philadelphia, Pa., 1982), pp. 385-397) or with HBsAg produced in yeast (devoid of pre-S gene coded sequences; W. J. McAleer, E. B. Buynak, R. F. Maigetter, D. E. Wambler, W. J. Miller, M. R. Hilleman, *Nature (London),* 307, 178 (1984)) did not develop detectable antibodies recognizing either of the two synthetic peptides. On the other hand, 7 out of 12 individuals who received a vaccine consisting of intact HBsAg developed these antibodies.

EXAMPLE 13

Figure 12:
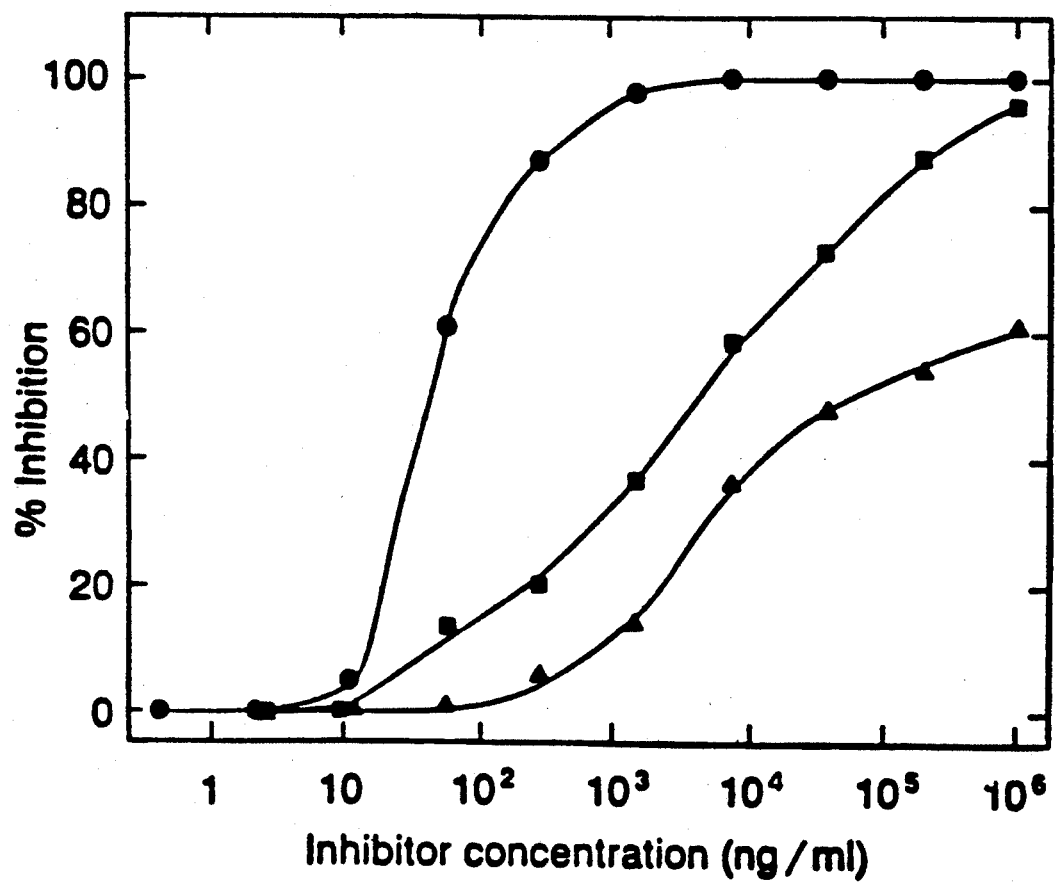
FIG. 12 shows a plot depicting the inhibition of the reaction of anti-pre-S(120-145) IgG (antiserum diluted 1:100) with a pre-S(120-145)-β-galactosidase conjugate by; free peptide pre-S(120-145) [○]; by 20 nm spherical HBsAg particles [△] and by HBV particles [□]. The latter two preparations contained the same concentration of HBsAG S-protein as determined by radioimmunoassay (AUSRIA, Abbott Laboratories).

Quantitative aspects of the immunological cross-reactivity between pre-S gene coded sequences exposed on HBV particles (or on HBsAg) and the synthetic peptide analogues were tested. The peptides were conjugated to β-galactosidase, and the inhibitory effect of free peptides, HBV and HBsAg, respectively, on the formation of immune complexes containing the enzyme-conjugated peptide was studied. Results shown in FIG. 12 indicate that HBV, at sufficient concentrations, inhibited completely the reaction between anti-pre-S(120-145) and pre-S(120-145)-β-galactosidase. HBsAg had <1/5 of the inhibitory activity corresponding to HBV. The inhibitory activity of pepsin-treated HBsAg was <1/1,000 of the activity corresponding to intact HBsAg. These results indicate the absence in the anti-pre-S(120-145) serum of a subpopulation of antibodies which recognize the synthetic peptide but not the native protein. Such antibody subpopulations are observed in many other antisera raised against synthetic peptide analogues of viral proteins. The concentration of free peptide sufficient for approximately 50% inhibition of the reaction of pre-S(120-145)-β-galactosidase with anti-pre-S(120-145) is approximately 1/100 of that for HBV on a weight basis (see FIG. 11). However, since the molecular weight of pre-S(120-145) is approximately 3 kD and the molecular weight of HBV protein components reacting with anti-pre-S(120-145) (representing a minor (<20%) portion of the total HBV mass) is between approximately 33 and approximately 67 kD, the molar concentrations of HBV and pre-S(120-145) required for this degree of inhibition are approximately the same. This indicates that the antigenic determinants on the peptide analogue and on the corresponding segment of the HBV envelope protein(s) are structurally closely related.

EXAMPLE 14

A peptide pre-S (94-117) (subtype adw$_2$) was synthesized according to the procedure described hereinabove in Example 2.

EXAMPLE 15

A rabbit was immunized with the peptide pre-S (94-117) prepared according to Example 14 and linked to a carrier according to the procedure of Example 7. Such immunization was conducted according to the procedure described hereinabove for Example 3 and was found to produce antibodies in the serum of the rabbit so inoculated. However, the antibody titers were substantially less than those observed for the use of pre-S (120-145) and pre-S (12-32).

EXAMPLE 16

A peptide pre-S (153-171) (subtype adw$_2$) was synthesized according to the procedure described hereinabove in Example 2.

EXAMPLE 17

A rabbit was immunized with the peptide pre-S (153-171) prepared according to Example 16 and linked to a carrier according to the procedure of Example 7. Such immunization was conducted according to the procedure described hereinabove for Example 3 and was found to produce antibodies in the serum of the rabbit so inoculated. However, the antibody titers were substantially less than those observed for the use of pre-S (120-145) and pre-S (12-32).

EXAMPLE 18

A peptide pre-S (1-21) (subtype adw$_2$) was synthesized according to the procedure described hereinabove in Example 2.

EXAMPLE 19

A rabbit was immunized with the peptide pre-S (1-21) prepared according to Example 18 and linked to a carrier according to the procedure of Example 7. Such immunization was conducted according to the procedure described hereinabove for Example 3 and was found to produce antibodies in the serum of the rabbit so inoculated. However, the antibody titers were substantially less than those observed for the use of pre-S (120–145) and pre-S (12–32).

EXAMPLE 20

A peptide pre-S (32–53) (subtype adw$_2$) was synthesized according to the procedure described hereinabove in Example 2.

EXAMPLE 21

A rabbit was immunized with the peptide pre-S (32–53) prepared according to Example 20 and linked to a carrier according to the procedure of Example 7. Such immunization was conducted according to the procedure described hereinabove for Example 3 and was found to produce antibodies in the serum of the rabbit so inoculated. However, the antibody titers were substantially less than those observed for the use of pre-S (120–145) and pre-S (12–32).

EXAMPLE 22

A peptide pre-S (57–73) (subtype adw$_2$) was synthesized according to the procedure described hereinabove in Example 2.

EXAMPLE 23

A rabbit was immunized with the peptide pre-S (57–73) prepared according to Example 22 and linked to a carrier according to the procedure of Example 7. Such immunization was conducted according to the procedure described hereinabove for Example 3 and was found to produce antibodies in the serum of the rabbit so inoculated. However, the antibody titers were substantially less than those observed for the use of pre-S (120–145) and pre-S (12–32).

EXAMPLE 24

Figure 13:
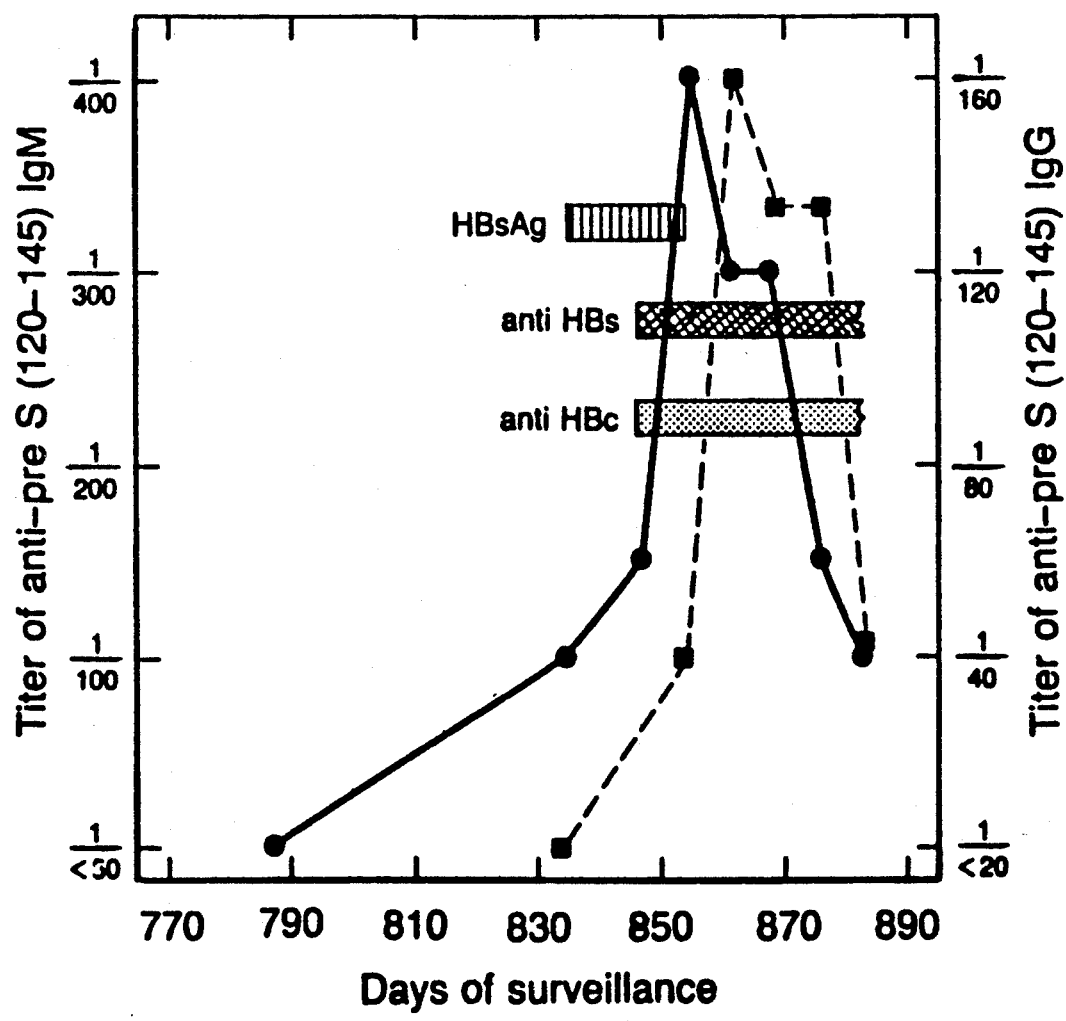
FIG. 13 depicts a plot of titers of anti-pre-S(120-145) antibodies versus days of surveillance and indicates the development of IgM [○] and IgG [□] antibodies to the pre-S gene coded protein of HBV during acute hepatitis B.

Detection of anti-pre-S protein antibodies in human sera using synthetic peptides As discussed above, antibodies recognizing synthetic peptide analogues of the pre-S protein were detected in sera of humans during recovery from hepatitis B (FIG. 11). The time course of development of antibodies recognizing pre-S(120–145) in a selected patient is shown in FIG. 13.

Anti-pre-S protein antibodies are detected in human sera early during acute hepatitis type B. IgM antibodies recognizing the peptides were detected during HBsAg antigenemia before antibodies to the S-protein (anti-HBs) or to hepatitis B core antigen (anti-HBc) were detectable. After development of the latter two antibodies, the level of antibodies with anti-pre-S specificity declined. Variations of this pattern of anti-pre-S development among patients with hepatitis B were observed. In some cases, antibodies recognizing the synthetic peptides were present even before HBsAg was detected in plasma, or when HBsAg never appeared in blood and the only marker for hepatitis B was anti-HBc and later anti-HBs.

Antibodies to pre-S(120–145) were measured by RIA. Similar results were obtained by assaying antibodies to pre-S(12–32). HBsAg, anti-HBs and antibodies to hepatitis B core antigen (anti-HBc) were assayed using commercial test kits (Abbot Laboratories, North Chicago, Ill.). The broken line at the end of bars corresponding to the different markers of HBV infection indicates positivity at the termination of surveillance. Antibody titers represent the highest dilution of serum at which radioactivity counts corresponding to the specimens divided by counts corresponding to equally diluted control serum were $\geq 2.1$.

Humans vaccinated with pepsin-treated HBsAg (Hilleman, M. R., Buynak, E. B., McAleer, W. J., McLean, A. A., Provost, P. J. & Tytell, A. A. in *Viral Hepatitis, 1981 International Sympsosium* (eds. Szmuness, W., Alter, H. J. & Maynard, J. E.) 385–397 (Franklin Institute Press, Philadelphia, Pa., 1982)), (pepsin treatment removes all anti-pre-S(120–145) reactive material), or with HBsAg produced in yeast (devoid of pre-S gene coded sequences (McAleer, W. J. Buynak, E. B. Maigetter, R. Z., Wambler, D. E., Miller, W. J., Hillemann, M. R. *Nature*, (London), 307, 178–180 (1984); did not develop detectable antibodies recognizing either of the two synthetic peptides. On the other hand, 7 out of 12 individuals who received a vaccine consisting of intact HBsAg (McAuliffe, V. J., Purcell, R. H., Gerin, J. L. & Tyeryar, F. J. in *Viral Hepatitis* (eds Szmuness, W., Alter, H. J. & Maynard, J. E.) 425–435, Franklin Institute Press, Philadelphia, Pa.) developed these antibodies. These 7 individuals also had the highest antibody response to the S-protein, as measured by the AUSAB test (Abbott), suggesting that a lack of detectable response to the pre-S protein was due to the sensitivity limits of the test. In this respect, it is of importance that the hepatitis B vaccine heretofore used, the production of which involves pepsin treatment of HBsAg, although highly efficient in apparently healthy individuals, has had low immunogencity and no protective effect in hemodialysis patients (Stevens, C. E., Alter, H. J., Taylor, P. E., Zang, E. A., Harley, E. J. & Szmuness, W., *N. Engl. J. Med.*, 311, 496–501 (1984)). Other vaccines produced without pepsin treatment do not seem to have this defect (Desmyter, J. in *Viral Hepatitis and Liver Disease* (eds Vyas, G. N., Dienstag, J. L. & Hoofnagle, J.), in press Grune and Stratton, Orlando, Fla. 1984).

EXAMPLE 25

RIA Tests of Preparations Containing HBV-specific Proteins

Figure 14:
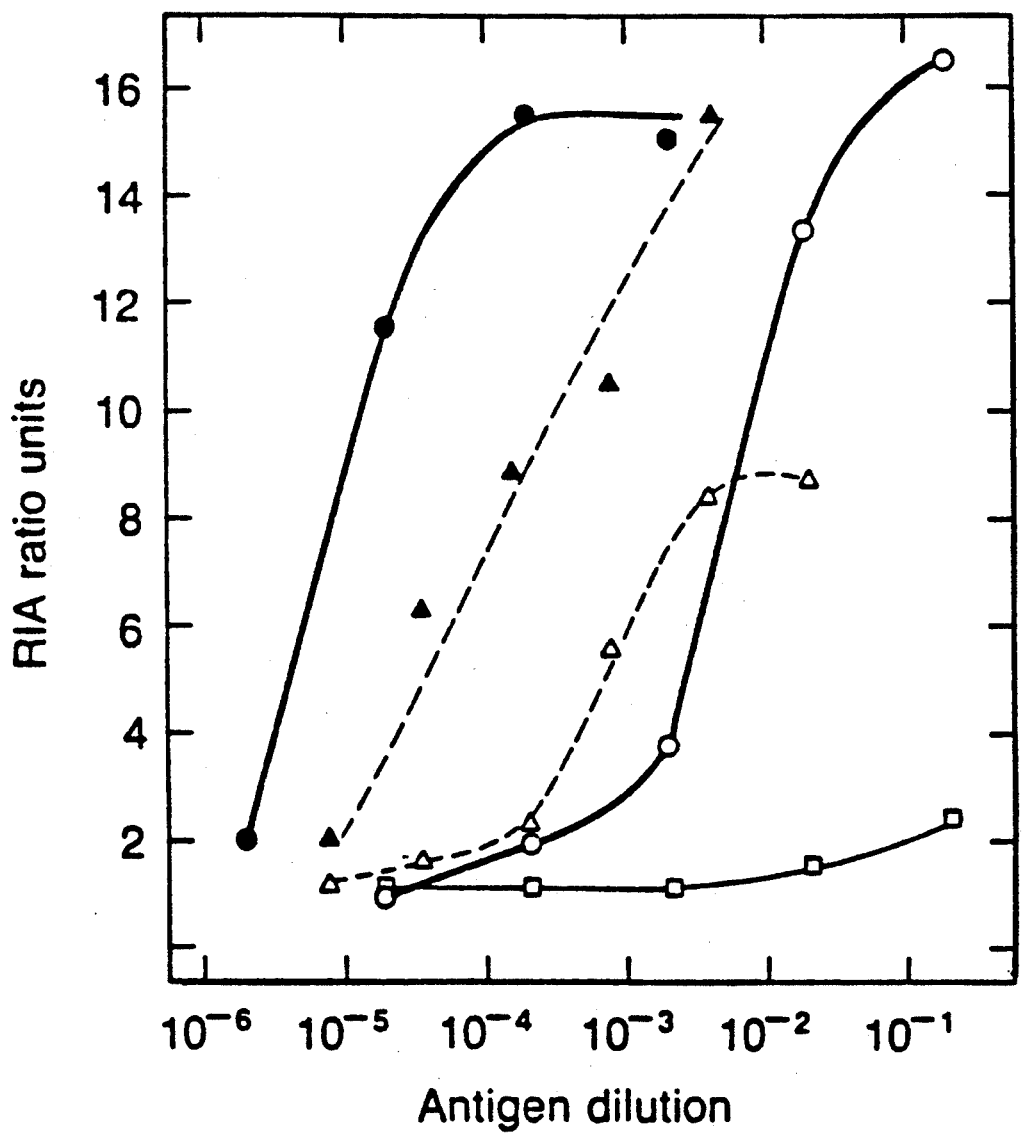
FIG. 14 shows a plot for radioimmunoassays of various preparations containing HBV-specific proteins on polystyrene beads coated either with anti-pre-S(120-145) IgG (○, ◯, □) or with IgG from a rabbit antiserum against HBV particles and tubular forms of HBsAg (▲, △). The tested antigens were: HBV particles and tubular forms (△, ▲); approximately 20 nm spherical particles of HBsAg isolated from plasma (○, ●); and the latter particles treated with pepsin (1 mg/ml HBsAG, 50 μg/ml pepsin in 0.1M glycine-HCL, pH 2.2, 2 hours at 37° C.) (□).
Figure 15:
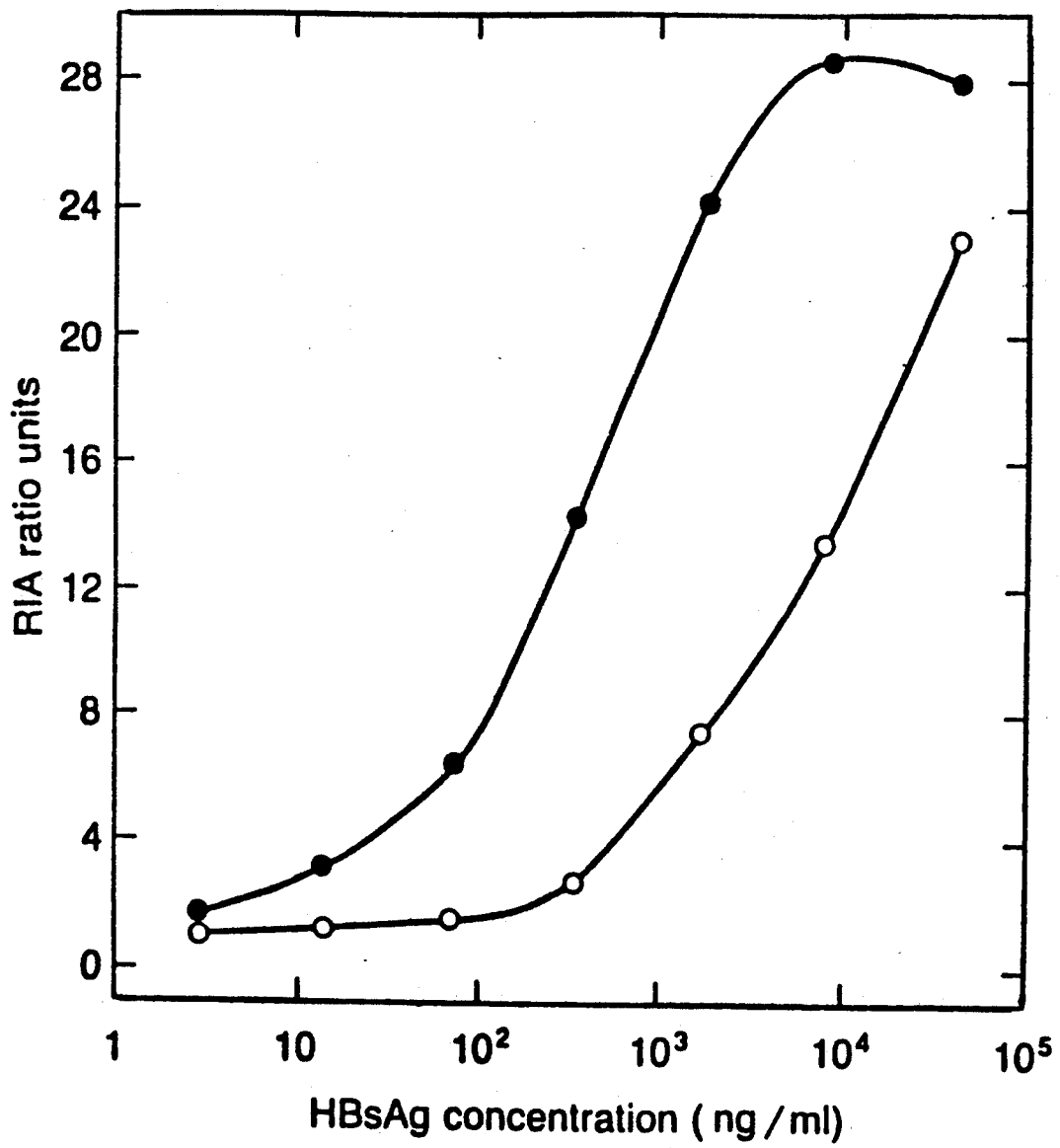
FIG. 15 depicts a plot for radioimmunoassays of polymerized albumin-binding sites associated with HBsAg isolated from human plasma and containing pre-S gene coded sequences ( ) or with HBsAg produced in yeast transfected with recombinant DNA containing the HBV DNA S-gene and thus lacking pre-S gene coded sequences (○).

Antibodies to the S-protein were removed from rabbit anti-serum against HBV particles by affinity chromatography (Neurath, A. R., Trepo, C., Chen, M., Prince, A. M., *J. Gen. Virol.*, 30, 277–285 (1976)—See FIG. 14. The tested antigens were: HBV particles and tubular forms (○, △); approximately 20 nm spherical particles of HBsAg isolated from plasma (◯,△); and the latter particles treated with pepsin (1 mg/ml HBsAg, 50 μg/ml pepsin in 0.1M glycine-HCl, pH 2.2, 2 hours at 37° C.) (□). The RIA tests were performed as described in Neurath, A. R., Kent, S. B. H., Strick, N., *Science*, 224, 392–395 (1984). The concentration of HBsAg S-protein was adjusted to the same level in all preparations tested as based on RIA tests (AUSRIA, Abbot Laboratories). HBV particles (contaminated with tubular forms of HBsAg) were concentrated from serum approximately 100× by centrifugation for 4 hours at 25,000 rpm in a Spinco 35 rotor. The concentrate (2 ml) was layered over a discontinuous gradient consisting of 11 ml of each 20, 10 and 5% sucrose (w/w) in 0.14M NaCl-0.01M Tris-0.02% NaN$_3$, pH 7.2 (TS) and centrifuged for 16 hours at 25,000 rpm in a Spinco rotor SW 27. The final pellet was resuspended in TS.

HBV particles were recognized much more efficiently than purified approximately 22 nm spherical particles in RIA tests based on polystyrene beads coated with either anti-pre-S(120–145) or with rabbit antibodies to HBV particles. Treatment of HBsAg with pepsin, a step used in preparing some current hepatitis B vaccines, resulted in an approximately $10^3$-fold decrease in reactivity with anti-pre-S(120–145). HBsAg from vaccines derived either from infected plasma (Hilleman, M. R., et al, 1982) supra), or produced in yeast McAleer et al (1984), supra), had $\leqq 1/5,000$ of the reactivity of intact HBsAg in these tests.

In reverse tests, beads coated with HBsAg, with HBV particles, with pepsin-treated HBsAg, or with HBsAg corresponding to the vaccines mentioned above were utilized. IgG antibodies (from different rabbit antisera to pre-S sequences) reacting with the beads were assayed based on the subsequent attachment of labeled anti-rabbit IgG. Positive results using anti-pre-S(120–145) were obtained only with beads coated with intact HBsAg or with HBV particles. Anti-pre-S(12–32) reacted exclusively with HBV-coated beads.

EXAMPLE 26

Involement of Pre-S Gene Coded HBV Domains In Attachment to Cell Receptors

It has been suggested that the 55 C-terminal amino acids of the pre-S protein mediate the attachment of HBsAg to human albumin polymerized by glutaraldehyde (pHSA) and that this attachment plays an essential role in the in vivo adsorption of HBV to hepatocytes (Machida, A. et al, *Gastroenterology,* 86, 910–918, (1984); Machida, A. et al, *Gastroenterology,* 85, 268–274, (1983). However, there is no compelling evidence to support the role of the pHSA-HBV interaction in infection of liver cells by HBV. In addition, both HBsAg containing or lacking these 55 amino acid residues react with pHSA (FIG. 15), albeit the reaction is enhanced by the presence of the pre-S gene coded sequences. The RIA tests involved in FIG. 15 were conducted as described in Neurath, A. R., Strick, N. *Intervirology,* 11, 128–132 (1979).

To explore directly the reaction of HBsAg with liver cells, an assay system based on the attachment of liver cells to insolubilized HBsAg was developed.

HBsAg (HBV) was attached to N-N'-p-phenylenedimaleimide-derivatized sulfhydryl cellulose under conditions described for linking of pre-S(120–145), as described above. About 4 mg of HBsAg was linked to 1 g of the cellulose derivative. A control cellulose derivative was prepared by linking bovine serum albumin to the activated matrix. Forty mg of the cellulose derivative suspended in TS containing 10 mg/ml of bovine serum albumin (TS-BSA) were mixed with approximately $2\times10^6$ washed Hep G2 human hepatoma cells (see Aden, D. P., Fogel, A., Plotkin, S., Damjanov, J., Knowles, B. B., *Nature* (London), 282, 615–617 (1979) suspended in TS-BSA and incubated for 30 min at 37° C., followed by 1 hour at 4° C. HeLa cells and Clone 9 normal rat liver cells (American Type Culture Collection) were used as controls. The cell-cellulose mixtures were layered on top of 1 ml of 33% (w/w) Hypaque and centrifuged for 2 minutes at 3,000 rpm. The cellulose derivative with attached cells pelleted under these conditions. Unattached cells recovered from the Hypaque-TS-BSA interphase were diluted 5-fold in TS-BSA and pelleted by centrifugation. The relative proportion of adsorbed and unadsorbed cells was determined by measurement of lactate dehydrogenase (LDH) activity in appropriate aliquots of cell lysates obtained after exposure to the detergent Triton X-100 (5 mg/ml in $H_2O$). LDH activity was determined using diagnostic kit No. 500 (Sigma).

Approximately 80 to 95% of human hepatoma Hep G2 cells (Aden, D. P. supra) attached to immobilized HBsAg in this assay. The attachment of control cells (HeLa, rat hepatocytes) was in the range of 10 to 20%. About 10% of Hep G2 cells attached to control cellulose. In the presence of anti-pre-S(120–145) and anti-pre-S(12–32) IgG (15 mg/ml), the adsorption of Hep G2 cells to HBsAg-cellulose decreased to 60 and 30%, respectively. A mixture of both antibodies (7.5 mg/ml of IgG each) caused a decrease of cell adsorption to 20%, indistinguishable from background levels.

Normal rabbit IgG, as well as antibodies to the S-protein (elicited by immunization with pepsin-treated HBsAg), failed to diminish the cell attachment, despite high levels of anti-HBs present in this serum (positive at a $10^{-6}$ dilution in the AUSAB test).

It will be appreciated that the instant specification and examples are set forth by way of illustration and not limitation and that various modifications and changes may be made without departing from the spirit and scope of the present invention.

What is claimed is:

1. A process for raising antibodies to the hepatitis B virus which comprises administering to an animal a protective amount of a peptide containing an amino acid chain of at least six consecutive amino acids within the pre-S gene coded region of the envelope of hepatitis B virus, said peptide not comprising a naturally occurring envelope protein of hepatitis B virus.

2. A hepatitis B vaccine comprising a protective amount of a peptide containing an amino acid chain of at least six consecutive amino acids within the pre-S gene coded region of the envelope of hepatitis B virus, said peptide not comprising a naturally occurring envelope protein of hepatitis B virus, and a physiologically acceptable diluent.

3. A hepatitis B vaccine according to claim 2, wherein said chain of amino acids is located within sequence position pre-S 120 to pre-S 174.

4. A hepatitis B vaccine according to claim 2, wherein said chain of amino acids comprises N-terminal methionine at sequence position pre-S 120.

5. A hepatitis B vaccine according to claim 2, wherein said chain of amino acids is located within sequence position pre-S 1 to pre-S 120.

6. A hepatitis B vaccine according to claim 2, wherein said peptide comprises a chain of at least 10 amino acids.

7. A hepatitis B vaccine according to claim 2, wherein said peptide comprises a chain of at least 15 amino acids.

8. A hepatitis B vaccine according to claim 2, wherein said peptide comprises a chain of at least 20 amino acids.

9. A hepatitis B vaccine according to claim 2, wherein said peptide comprises a chain of at least 26 amino acids.

10. A hepatitis B vaccine according to claim 2, wherein said chain is located within sequence position pre-S 15 to pre-S 120.

11. A hepatitis B vaccine according to claim 2, wherein said chain is located within sequence position pre-S 15 to pre-S 55.

12. A hepatitis B vaccine according to claim 2, wherein said chain is located within sequence position pre-S 90 to pre-S 120.

13. A hepatitis B vaccine according to claim 2, wherein said chain is located within sequence position pre-S 10 to pre-S 40.

14. A hepatitis B vaccine according to claim 2, wherein said chain comprises amino acids in the ayw subtype of the pre-S region.

15. A hepatitis B vaccine according to claim 2, wherein said chain comprises amino acids in the adyw subtype of the pre-S region.

16. A hepatitis B vaccine according to claim 2, wherein said chain comprises amino acids in the adw2 subtype of the pre-S region.

17. A hepatitis B vaccine according to claim 2, wherein said chain comprises amino acids in the adw subtype of the pre-S region.

18. A hepatitis B vaccine according to claim 2, wherein said chain comprises amino acids in the adr subtype of the pre-S region.

19. A hepatitis B vaccine according to claim 2, wherein said vaccine is free of any serum proteins.

20. A hepatitis B vaccine according to claim 2, wherein said chain is MQWNSTAFHQTLQPRVRGLYLPAGG.

21. A hepatitis B vaccine according to claim 2, wherein said chain is MGTNLSVPNPLGFFPDHQLDP.

22. A hepatitis B vaccine according to claim 2, wherein said chain is PAFGANSNNPDWFNPVKDDWP.

23. A hepatitis B vaccine according to claim 2, wherein said chain is PQAMQWNSTAFHQTLQDP.

24. A hepatitis B vaccine according to claim 2, wherein said chain is PASTNRQSGRQPTPISPPLRDSHP.

25. A hepatitis B vaccine according to claim 2, wherein said chain is PAPNIASHISSISARTGDP.

26. A hepatitis B vaccine according to claim 2, wherein said chain is MGGWSSKPRKGMGTNLSVPNP.

27. A hepatitis B vaccine according to claim 2, wherein said chain is PAFGANSNNPDWDFNPVKDDWP.

28. A hepatitis B vaccine according to claim 2, wherein said chain is QVGVGAFGPRLTPPHGG.

29. A hepatitis B vaccine according to claim 2, wherein said chain is MGGWSSKPRKG.

30. A hepatitis B vaccine according to claim 2, wherein said chain is MGGWSSKPRQG.

31. A hepatitis B vaccine according to claim 2, wherein said peptide does not comprise an amino acid sequence corresponding to the entire S gene coded region of the env gene product of hepatitis B virus.

32. A hepatitis B vaccine according to claim 2, wherein said peptide has no more than 100 amino acids.

33. A hepatitis B vaccine according to claim 2, wherein said peptide has no more than 40 amino acids.

34. A hepatitis B vaccine according to claim 2, wherein said peptide has no more than 30 amino acids.

35. A hepatitis B vaccine according to claim 2, wherein said peptide induces the formation of neutralizing antibodies to hepatitis B virus in a human.

36. A hepatitis B vaccine according to claim 2, wherein said peptide is linked to a carrier.

37. A hepatitis B vaccine according to claim 36, wherein said peptide is covalently linked to a carrier.

38. A hepatitis B vaccine according to claim 37, wherein said peptide is covalently linked to a lipid vesicle carrier.

39. A hepatitis B vaccine according to claim 38, wherein said lipid vesicle is stabilized by cross-linking.

40. A hepatitis B vaccine according to claim 2, wherein said chain is pre-S(120–145).

41. A hepatitis B vaccine according to claim 2, wherein said chain is pre-S(12–32).

42. A hepatitis B vaccine according to claim 2, wherein said chain is pre-S(117–134).

43. A hepatitis B vaccine according to claim 2, wherein said chain is pre-S(94–117).

44. A hepatitis B vaccine according to claim 2, wherein said chain is pre-S(153–171).

45. A hepatitis B vaccine according to claim 2, wherein said chain is pre-S(1–21).

46. A hepatitis B vaccine according to claim 2, wherein said chain is pre-S(57–73).

47. A method of protecting a human against becoming infected with hepatitis B comprising administering to said human an effective dosage of a vaccine according to claim 2.

48. A method of enhancing the humoral immune response to an S region immunogen encoded by the hepatitis B virus genome in an animal that exhibits a low response to said immunogen, which method comprises introducing into said animal an effective amount of a vaccine comprising a physiologically tolerable diluent that comprises dispersed therein a potentiating amount of a pre-S(2) region polypeptide encoded by said viral genome that is chemically coupled to an S region polypeptide immunogen which induces a protective response in an animal that exhibits a response to a S-region-containing immunogen.

49. The method of claim 48, wherein said S region polypeptide immunogen comprises the amino acid residue sequence of HBsAg from position 110 to position 137, from the amino-terminus thereof.

50. The method of claim 49, wherein the S region polypeptide immunogen is a polypeptide comprising an amino acid residue sequence of HBsAg from position 110 to position 137, from the amino-terminus thereof.

51. A method of enhancing the humoral immune response to an S region immunogen encoded by the hepatitis B virus genome in an animal that exhibits a low response to said immunogen, which method comprises introducing into said animal an effective amount of a vaccine constituted by a physiologically tolerable diluent that comprises dispersed therein a potentiating amount of a pre-S(2) region polypeptide encoded by said viral genome that is chemically coupled to an S region immunogen which induces a protective response in an animal that exhibits a response to an S region-containing immunogen, wherein said S region immunogen is an amino acid residue sequence of HBsAg from position 110 to position 137, from the amino-terminus thereof, and wherein said coupled pre-S(2) region polypeptide is in addition to any of said 55-residue polypeptide present in said S region immunogen.

52. A method of protecting a human against becoming infected with hepatitis B virus comprising administering to said human an effective dosage of a vaccine which comprises a peptide comprising an amino acid chain of at least six consecutive amino acids within the pre-S gene coded region of the envelope of hepatitis B virus.

* * * * *